US012415014B2

(12) United States Patent
Hossain et al.

(10) Patent No.: US 12,415,014 B2
(45) Date of Patent: Sep. 16, 2025

(54) ANTIBACTERIAL NANOFIBRES

(71) Applicant: ConvaTec Technologies Inc., Las Vegas, NV (US)

(72) Inventors: Mohammad Forhad Hossain, Dacca (BD); Hugh R. Gong, Greater Manchester (GB); Lucy Ballamy, Wales (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 0 days.

(21) Appl. No.: 15/570,276

(22) PCT Filed: Apr. 28, 2016

(86) PCT No.: PCT/US2016/029862
§ 371 (c)(1),
(2) Date: Oct. 27, 2017

(87) PCT Pub. No.: WO2016/176495
PCT Pub. Date: Nov. 3, 2016

(65) Prior Publication Data
US 2018/0133359 A1  May 17, 2018

Related U.S. Application Data

(60) Provisional application No. 62/154,056, filed on Apr. 28, 2015.

(51) Int. Cl.
A61L 15/26 (2006.01)
A61L 15/28 (2006.01)
A61L 15/44 (2006.01)
A61L 15/46 (2006.01)
C08L 5/04 (2006.01)
C08L 71/02 (2006.01)
A61L 15/62 (2006.01)

(52) U.S. Cl.
CPC .............. *A61L 15/46* (2013.01); *A61L 15/28* (2013.01); *A61L 15/44* (2013.01); *C08L 71/02* (2013.01); *A61L 15/62* (2013.01); *A61L 2300/404* (2013.01); *A61L 2300/802* (2013.01); *A61L 2400/12* (2013.01)

(58) Field of Classification Search
CPC .............. A61L 15/28; A61L 2300/404; A61L 2300/802; A61L 2400/12; A61L 15/46; A61L 15/240012; C08L 71/02; C08L 5/04
See application file for complete search history.

(56) References Cited

U.S. PATENT DOCUMENTS

| 5,792,090 | A | * | 8/1998 | Ladin | A61L 15/18 424/449 |
|---|---|---|---|---|---|
| 6,753,454 | B1 | | 6/2004 | Smith et al. | |
| 11,026,847 | B2 | | 6/2021 | Piotrowski et al. | |
| 11,090,409 | B2 | | 8/2021 | Zimnitsky et al. | |
| 11,191,810 | B2 | | 12/2021 | Gronberg et al. | |
| 11,191,866 | B2 | | 12/2021 | Bouvier et al. | |
| 11,207,442 | B2 | | 12/2021 | Locke et al. | |
| 11,266,537 | B2 | | 3/2022 | Robinson et al. | |
| 11,278,638 | B2 | | 3/2022 | Nisbet | |
| 11,318,223 | B2 | | 5/2022 | Wibaux | |
| 11,364,152 | B2 | | 6/2022 | Robinson et al. | |
| 11,730,876 | B2 | | 8/2023 | Phillips et al. | |
| 11,850,351 | B2 | | 12/2023 | Robinson et al. | |
| 11,896,733 | B2 | | 2/2024 | Zimnitsky et al. | |
| 11,931,226 | B2 | | 3/2024 | Collinson et al. | |
| 2002/0081930 | A1 | | 6/2002 | Jackson et al. | |
| 2005/0008776 | A1 | | 1/2005 | Chhabra et al. | |
| 2005/0053784 | A1 | * | 3/2005 | Wood | D01F 6/06 604/367 |
| 2006/0003654 | A1 | * | 1/2006 | Lostocco | A61K 8/0208 442/149 |
| 2009/0112170 | A1 | * | 4/2009 | Wells | A61M 35/003 604/290 |
| 2009/0324893 | A1 | | 12/2009 | Jens et al. | |
| 2010/0018641 | A1 | | 1/2010 | Branham et al. | |
| 2010/0021552 | A1 | * | 1/2010 | Hayes | A61L 15/46 424/618 |
| 2012/0141558 | A1 | | 6/2012 | Zhang et al. | |
| 2013/0218336 | A1 | | 8/2013 | David et al. | |
| 2014/0335200 | A1 | | 11/2014 | Zhang et al. | |
| 2016/0339227 | A1 | | 11/2016 | Tsai | |

(Continued)

FOREIGN PATENT DOCUMENTS

CN 102505461 A 6/2012
EP 3250244 A0 12/2017
(Continued)

OTHER PUBLICATIONS

Sigma, Triton X-100, obtained online at https://www.snowpure.com/docs/triton-x-100-sigma.pdf, pp. 1-2. (Year: 2002).*
Aytac, Electrospinning of Biocompatible Polymeric Nanofibers Functionalized with Cyclodextrin Inclusion Complex, Bilkent University, pp. 1-112. (Year: 2012).*
Kayaci, Fatma, Zeynep Aytac, and Tamer Uyar. "Surface modification of electrospun polyester nanofibers with cyclodextrin polymer for the removal of phenanthrene from aqueous solution." Journal of hazardous materials 261 (2013): 286-294. (Year: 2013).*
PCT/US2016/029862 International Search Report and Written Opinion dated Jul. 28, 2016.
European Patent Application No. 16787182.1 Extended European Search Report dated Dec. 5, 2018.
(Continued)

*Primary Examiner* — Abigail Vanhorn
(74) *Attorney, Agent, or Firm* — Taft Stettinius & Hollister LLP; Ryan O. White; Derek B. Lavender

(57) ABSTRACT

Antibacterial nanofibres and methods for their preparation are described. Antibacterial nanofibres include as-spun alginate nanofibres treated with silver to generate silver-alginate nanofibres. Antibacterial nanofibres provided are useful components of wound dressings, wherein the wound dressings optionally further comprise malodor absorbing agents such as cyclodextrins.

5 Claims, 12 Drawing Sheets

(56) References Cited

U.S. PATENT DOCUMENTS

| | | |
|---|---|---|
| 2021/0177663 A1 | 6/2021 | Robinson et al. |
| 2021/0228768 A1 | 7/2021 | Um et al. |
| 2021/0275693 A1 | 9/2021 | Ballamy |
| 2021/0338885 A1 | 11/2021 | Zimnitsky et al. |
| 2021/0361492 A1 | 11/2021 | Wibaux et al. |
| 2022/0142822 A1 | 5/2022 | Cotton |
| 2024/0082477 A1 | 3/2024 | Robinson et al. |

FOREIGN PATENT DOCUMENTS

| | | | |
|---|---|---|---|
| EP | 3288600 A1 | 3/2018 | |
| EP | 3315145 A1 | 5/2018 | |
| EP | 3446665 A1 | 2/2019 | |
| EP | 3672543 A0 | 7/2020 | |
| EP | 3687467 A0 | 8/2020 | |
| EP | 3858392 A1 | 8/2021 | |
| EP | 3274002 A0 | 9/2021 | |
| EP | 3142615 A0 | 2/2022 | |
| EP | 3060264 B1 | 4/2022 | |
| EP | 2767305 B2 | 4/2024 | |
| GB | 2416781 A | 2/2006 | |
| WO | WO-9222285 A1 | 12/1992 | |
| WO | 0209782 A1 | 2/2002 | |
| WO | 2006108364 A1 | 10/2006 | |
| WO | 2009141633 A2 | 11/2009 | |
| WO | 2013165975 A1 | 11/2013 | |
| WO | 2014020131 A1 | 2/2014 | |
| WO | WO-2014066297 A1 * | 5/2014 | ............. A61L 15/22 |
| WO | WO-2016176495 A1 | 11/2016 | |

OTHER PUBLICATIONS

Aytac et al.: "Release and antibacterial activity of allyl isothiocyanate/[beta]-cyclodextrin complex encapsulated in electrospun nanofibers," Colloids and Surfaces B: Biointerfaces, vol. 120, pp. 125-131 (2014).

Wang Shan et al.: "Functionalization of electrospun [beta]-cyclodextrin/polyacrylonitrile (PAN) with silver nanoparticles: Broad-spectrum antibacterial property," Applied Surface Science, vol. 261, pp. 499-503 (2012).

Australian Application No. 2016256436 Examination Report No. 1 dated Oct. 9, 2019.

European Examination Report; European Patent Office; European Patent Application No. 16787182.1; Feb. 17, 2020; 5 pages.

Shan Wang et al.; Functionalization of Electrospun B-Cyclodextrin/Polyacrylonitrile (PAN) with Silver Nanoparticles: Broad-Spectrum Antibacterial Property; Applied Surface Science; 2012; 5 pages; vol. 261.

Zeynep Aytac et al.; Release and Antibacterial Activity of Allyl Isothiocyanata/B-Cyclodextrin Complex Encapsulated in Electrospun Nanofibers; Colloids and Surfaces B: Biointerfaces; 2014; 7 pages; vol. 120.

Akhmetova, Alma et al., A Comprehensive Review of Topical Odor-Controlling Treatment Options for Chronic Wounds, Wound, Ostomy and Continence Nurses Society, Dec. 2016, vol. 43, No. 6, pp. 598-609, Lippincott Williams & Wilkins.

European Examination Report in EP 23193492.8, 3 pages, dated Mar. 5, 2025.

* cited by examiner

ANTIBACTERIAL NANOFIBRES

CROSS-REFERENCE

This application is the U.S. National Phase entry of International Application No. PCT/US2016/029862, filed on Apr. 28, 2016, which claims the benefit of U.S. Provisional Application No. 62/154,056, filed Apr. 28, 2015, each of which are incorporated herein by reference in their entireties.

BACKGROUND OF THE INVENTION

An important problem associated with wound treatment is the management of infection. Infection can retard wound healing, is traumatic for the patient and can significantly increase treatment time and cost. Consequently there is a need to both prevent and treat infection resulting from wounds, preferably in conjunction with wound dressings.

SUMMARY OF THE INVENTION

Disclosed herein are methods and compositions for wound treatment in a subject including the preparation and use of compositions comprising antimicrobial agents incorporated with or coating nanofibre materials. In other embodiments, the methods and compositions incorporate an anti-odor component with the nanofibre material. In yet other embodiments, the methods and compositions incorporate both an antimicrobial and anti-odor component with the nanofibre material.

In one aspect, provided herein are methods for preparing anti-odor, antimicrobial nanofibres derived from alginate nanofibres, the method comprising a) contacting the alginate nanofibres with a first organic solution comprising calcium ions to generate calcium-alginate nanofibres; b) contacting the calcium-alginate nanofibres with a second organic solution comprising an antimicrobial agent to generate antimicrobial-alginate nanofibres; and c) combining or coating the antimicrobial-alginate nanofibres with a malodor absorbing agent to generate anti-odor, antimicrobial nanofibres. In some embodiments, the alginate nanofibres are formed by electrospinning an aqueous solution comprising from 1% to 10% by weight mixture of alginate and poly(ethylene)oxide (PEO), for example, 4% mixture of alginate and PEO. In some embodiments, the aqueous solution comprises an alginate to PEO ratio from 60:40 to 80:20, for example, 70:30. In some embodiments, the first organic solution comprises from 0.1% to 10% by weight calcium salt. For example, calcium salts include, without limitation, calcium chloride, calcium bromide, calcium fluoride, calcium iodide, calcium nitrate and calcium hydride salts. In some embodiments, the antimicrobial agent comprises silver, acetic acid, chlorhexidine, iodine, hydrogen peroxide, sodium hypochlorite, potassium permanganate, triclosan, an antibiotic, or a combination thereof. Antibiotics include, without limitation, gentamicin, ofloxacin, minocycline, tetracycline, metronidazole and derivatives thereof. In some embodiments, the second organic solution comprises from 0.05% to 10% by weight silver salt. Silver salts include, without limitation, silver nitrate, silver chloride, silver sulfate, silver lactate, silver bromide, silver acetate, and combinations thereof. In some embodiments, the antimicrobial-alginate nanofibres are coated with a malodor absorbing agent by electrospraying, electrospinning, or both electrospraying and electrospinning the malodor absorbing agent onto a surface of the antimicrobial-nonofibres. In some embodiments, the malodor absorbing agent comprises cyclodextrin. In some instances, the method comprises washing the alginate nanofibres with an organic solvent prior to contact with the first organic solution. In some instances, the method comprises washing the antimicrobial-alginate nanofibres with an organic solvent prior to combining or coating with the malodor absorbing agent. In some instances, the anti-odor, antimicrobial nanofibres have less than a 10% decrease in average fibre diameter as compared to the average fibre diameter of the alginate nanofibres. In some embodiments, at least a portion of the antimicrobial agent of the anti-odor, antimicrobial nanofibres dissociates and releases from the anti-odor, antimicrobial nanofibres when the anti-odor, antimicrobial nanofibres are in contact with wound exudate. In some embodiments, at least a portion of calcium ions of the anti-odor, antimicrobial nanofibres dissociates and releases from the anti-odor, antimicrobial nanofibres when the anti-odor, antimicrobial nanofibres are in contact with wound exudate. In some instances, the anti-odor antimicrobial nanofibres remain intact after soaking in an aqueous solution for 24 hours.

In one aspect, provided herein are anti-odor, antimicrobial nanofibres comprising alginate nanofibres electrospun from an aqueous solution comprising a 4% mixture of alginate and PEO in a 70:30 ratio; an antimicrobial agent; and a malodor absorbing agent. In some embodiments, the antimicrobial agent comprises silver, acetic acid, chlorhexidine, iodine, hydrogen peroxide, sodium hypochlorite, potassium permanganate, triclosan, an antibiotic, or a combination thereof. In some instances, the malodor absorbing agent comprises silver ions. In some cases, at least a portion of the silver ions form particles within the anti-odor, antimicrobial nanofibres. In some cases, the silver particles have an average diameter from 150 nm to 300 nm. In some cases, at least a portion of the silver ions in anti-odor, antimicrobial nanofibres dissociate and release from the anti-odor, antimicrobial nanofibres when contacted with wound exudate. In some embodiments, the anti-odor, antimicrobial nanofibres further comprise calcium ions. In some cases, at least a portion of the calcium ions dissociate and release when the anti-odor, antimicrobial nanofibres are contacted with wound exudate. In some embodiments, the malodor absorbing agent of the anti-odor, antimicrobial nanofibres is in the form of a fibre. In some embodiments, the malodor absorbing agent is electrospun onto the alginate nanofibres. In some embodiments, the malodor absorbing agent is electrosprayed onto the alginate nanofibres. In some embodiments, the malodor absorbing agent comprises cyclodextrin. In some examples, the cyclodextrin comprises hydroxypropyl-β-cyclodextrin (HB-β-CD). In some cases, the anti-odor, antimicrobial nanofibres do not comprise PEO. In some cases, the average nanofibre diameter of anti-odor, antimicrobial nanofibres is from 120 nm to 150 nm. In some instances, the anti-odor, antimicrobial nanofibres remain intact after soaking in an aqueous solution for 24 hours. In another aspect, provided herein is a wound dressing structure comprising anti-odor, antimicrobial nanofibres and a backing. In some embodiments, the backing is a fabric backing. In some embodiments, the backing is nylon. In some embodiments, the backing comprises carboxymethylcellulose (CMC).

In a further aspect, provided herein is a method of preparing a wound dressing structure, the method comprising: depositing alginate nanofibres on a surface of a backing, b) chemically treating the alginate nanofibres with a solution comprising calcium ions dissolved in an organic solvent to generate calcium-alginate nanofibres, c) chemically treating the calcium-alginate nanofibres with a solution comprising an antimicrobial agent dissolved in an organic solvent to generate antimicrobial-alginate nanofibres, and d) electrospinning or electrospraying fibres comprising a malodor absorbing agent onto a surface of the antimicrobial-alginate nanofibres. In some embodiments, the alginate nanofibres are deposited on the surface of the backing by electrospinning an aqueous solution comprising from 1% to 10% by weight mixture of alginate and PEO. In some embodiments, the aqueous solution comprises an alginate to PEO ratio from 60:40 to 80:20. In some embodiments, the solution comprising calcium ions comprises from 0.1% to 10% by weight calcium salt. Calcium salts include, without limitation, calcium chloride, calcium bromide, calcium fluoride, calcium iodide, calcium nitrate, and calcium hydride. In some embodiments, the antimicrobial agent comprises silver, acetic acid, chlorhexidine, iodine, hydrogen peroxide, sodium hypochlorite, potassium permanganate, triclosan, an antibiotic, or a combination thereof. Antibiotics include, without limitation, gentamicin, ofloxacin, minocycline, tetracycline, metronidazole and derivatives thereof. In some instances, the solution comprising the antimicrobial agent comprises from 0.05% to 10% by weight silver salt. Silver salts include, without limitation, silver nitrate, silver chloride, silver sulfate, silver lactate, silver bromide, silver acetate, and combinations thereof. In some cases, the malodor absorbing agent comprises cyclodextrin. In some embodiments, the method further comprises washing the alginate nanofibres with an organic solvent after depositing onto the surface of the backing. In some cases, the method further comprises washing the antimicrobial-alginate nanofibres with an organic solvent prior to electrospinning or electrospraying with the malodor absorbing agent. In some cases, the antimicrobial-alginate nanofibres have less than a 10% decrease in average fibre diameter as compared to the average fibre diameter of the starting alginate nanofibre material. In some embodiments, a portion of the antimicrobial agent dissociates and releases from the wound dressing structure when the wound dressing structure is in contact with wound exudate. In some embodiments, a portion of the calcium ions dissociate and release from the wound dressing structure when the wound dressing structure is in contact with wound exudate. In some embodiments, the backing is a fabric backing. In some instances, the backing is nylon. In some instances, the backing comprises carboxymethylcellulose (CMC). In yet other embodiments, the backing comprises derivatized carboxymethylcellulose. Further provided, in one aspect, is a nanofibrous structure prepared by a method provided herein.

DETAILED DESCRIPTION OF THE INVENTION

Figure 1:
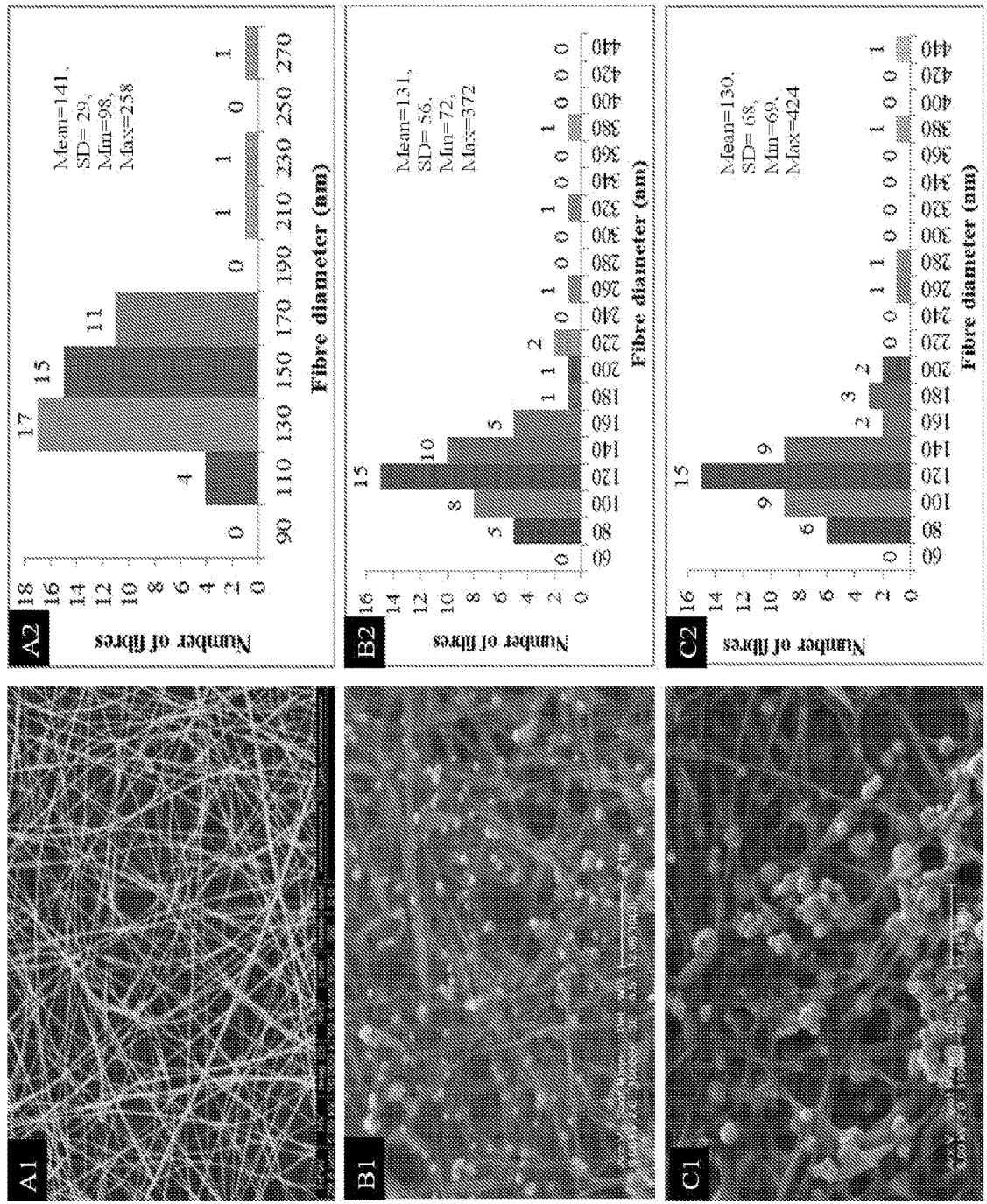
FIG. 1 shows scanning electron microscope images of as-spun sodium-alginate nanofibres before and after chemical treatment; and corresponding fibre diameter distributions.
Figure 1:
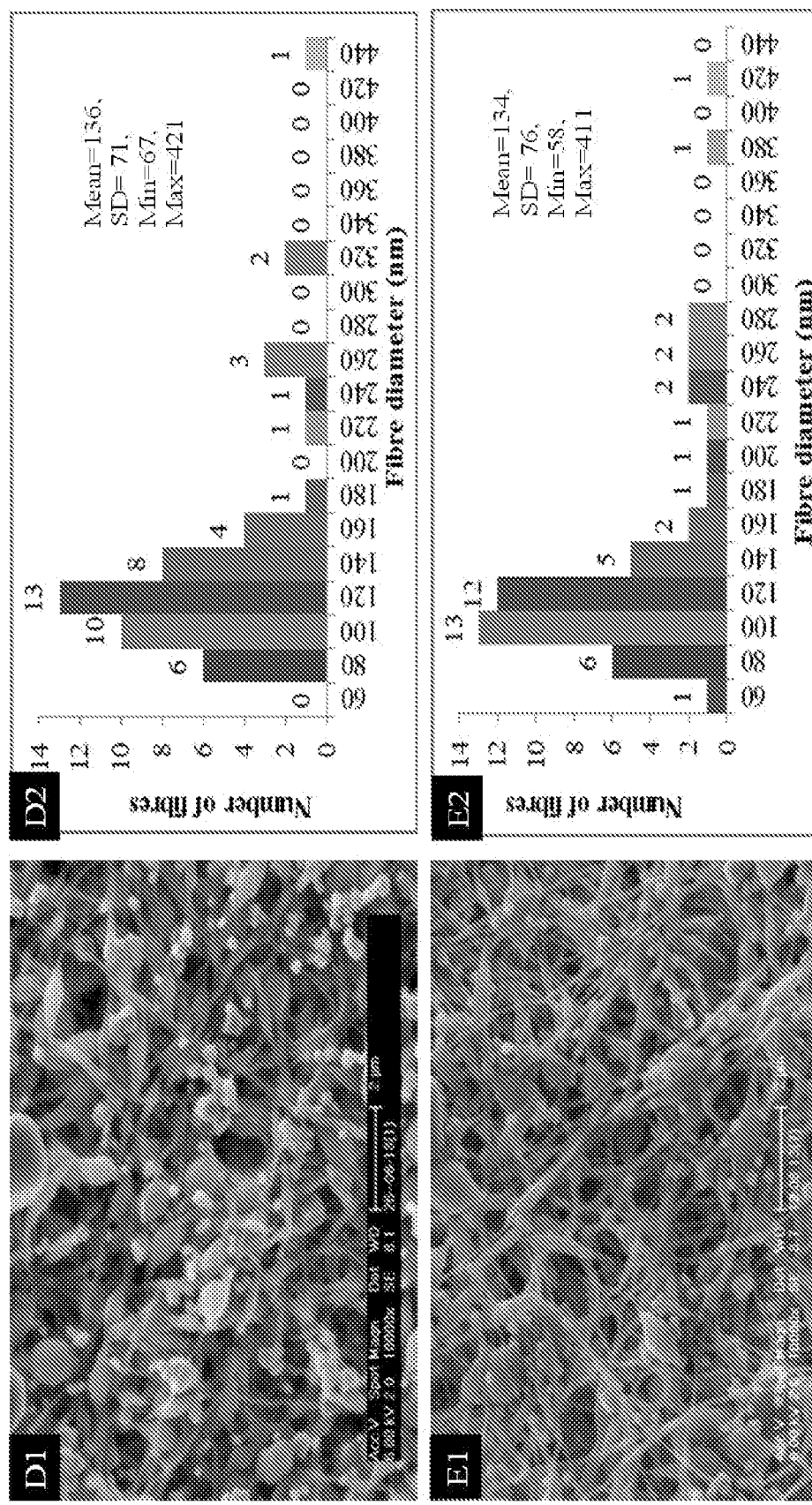

Provided herein, in various embodiments, are nanofibres chemically treated with an antibacterial agent to generate antibacterial nanofibres. A suitable antibacterial agent is silver, which in its ionic form, is an effective antimicrobial against a large number of gram-negative and gram-positive bacteria, including antibiotic-resistant strains such as methicillin-resistant and vancomycin-resistant *Staphylococcus aureaus* and *Enterococcus faecium*.

The antibacterial nanofibres described are useful as components of a wound dressing. In some embodiments, antibacterial nanofibres are prepared by treating nanofibres comprising biopolymers with an antibacterial agent. As an example, nanofibres are electrospun from a solution comprising one or more biopolymers and subsequently treated with an antibacterial agent. An exemplary biopolymer is alginate. Alginate is useful in a wound dressing to absorb large amounts of wound fluid while forming a gel-like substance, thus maintaining a moist microenvironment for the wound. In exemplary embodiments, antibacterial nanofibres are derived from as-spun nanofibres, wherein the as-spun nanofibres are formed by electrospinning a solution comprising a biopolymer and optionally a carrier polymer and/or a surfactant. In some embodiments, the as-spun nanofibres are formed by electrospinning a solution comprising alginate and a carrier polymer. In some cases, the carrier polymer is poly(ethylene)oxide (PEO).

In various embodiments, antibacterial nanofibres are derived from a nanofibre comprising a biopolymer suitable for end-use in a wound dressing. In some embodiments, nanofibres comprise biopolymers combined with one or more carrier polymers or carrier agents. Non-limiting examples of biopolymers and/or carriers useful as components of a nanofibre described herein include alginate, chitosan, carboxymethylcellulose (CMC), dextran, collagen, glycosaminoglycans, cellulose, poly(caprolactone), polyglactin, gelatin, PEO, polyvinyl alcohol, polyvinyl caprolactam, polyvinyl acetate, polyethylene glycol, cellulose derivatives, polyvinylpyrrolidone, poly-L-lactic acid, poly (E-caprolactone), chitosan, derivatives thereof, solutions thereof, and any combination thereof. In some instances, a solution comprising a biopolymer or biopolymer and carrier is electrospun with a surfactant, for example, oxtoxynol (Triton™ X-100), polysorbate (Tween™), stearyl alcohol, sorbitan, polyglycerol polyricinoleate, poloxamer, pentaethylene glycol monododecyl ether, oleyl alcohol, octyl glucoside, N-octyl beta-D-thioglycopyranoside, octaethylene glycol monododecyl ether, NP-40, nonoxynols, NONIDET P-40® (octylphenoxypolyethoxyethanol), monolaurin, ethoxylate, lauryl glucoside, isoceteth-20, IGEPAL CA-630® (octylphenoxypolyethoxyethanol), decyl glucoside, cetomacrogol, cetostearyl alcohol, cetyl alcohol, cocamide DEA, cocamide MEP, or derivatives or combinations thereof.

In various embodiments, nanofibres are produced from an organic solution comprising a biopolymer and optionally a carrier and/or surfactant. In alternative embodiments, nanofibres are produced from an aqueous solution comprising a biopolymer and optionally a carrier and/or surfactant. In other embodiments, nanofibres are produced from a miscible aqueous-organic solution comprising a biopolymer and optionally a carrier and/or surfactant.

In some examples, nanofibres are produced by electrospinning a solution comprising from about 1% to about 50% by weight biopolymer. In some examples, nanofibres are produced by electrospinning a solution comprising from about 1% to about 50% by weight biopolymer and carrier. In some instances, the percentage by weight of biopolymer or biopolymer:carrier in the solution is from about 1% to about 50%, from about 1% to about 40%, from about 1% to about 30%, from about 1% to about 20%, from about 1% to about 10%. In some instances, the percentage by weight of biopolymer or biopolymer:carrier in the solution is 1%, 2%, 3%, 4%, 5%, 6%, 7%, 8%, 9%, or 10%. For nanofibres produced from electrospinning solutions comprising a biopolymer and a carrier, the ratio of biopolymer to carrier may be from about 20:80 to about 95:5, from about 30:70 to about 95:5, from about 40:70 to about 95:5, from about 50:70 to about 95:5, from about 60:80 to about 90:10, from about 60:80 to about 80:20. In some embodiments, the ratio of biopolymer to carrier in an electrospinning solution is 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, or 80:20. In some implementations, nanofibres are electrospun from a 1% to 50% by weight solution of biopolymer and carrier polymer in a ratio from about 20:80 to about 95:5 biopolymer:carrier polymer. For example, the electrospun or as-spun nanofibres are produced by electrospinning a 4% by weight 70:30 biopolymer:carrier polymer solution. The as-spun nanofibres may comprise from about 20% to about 95%, preferably 50 to 90%, more preferably 60% to 80%, e.g., 70% biopolymer. In one embodiment, the as-spun nanofibres comprise from about 60% to about 80% or about 70% alginate or salt thereof. The as-spun nanofibres may comprise 5% to 80%, preferably 10% to 50%, more preferably 20% to 40%, e.g., 30% carrier polymer. In one embodiment, the as-spun nanofibres comprise from about 20% to about 40%, e.g., 30% PEO. In one example, nanofibres are produced by electrospinning a 4% by weight 70:30 alginate:carrier polymer solution, wherein the carrier polymer is optionally PEO and the solution optionally comprises a surfactant such as Triton™ X-100.

In some embodiments, the carrier is substantially removed from the nanofibres, for example, by washing the nanofibres with a solution suitable for maintaining the nanofibres insoluble, e.g., a solution comprising an organic solvent. The carrier is substantially removed, for example, when more than 90%, more than 92%, more than 94%, more than 96%, or more than 98% of the carrier is removed from the nanofibres or when the carrier is unable to be detected by spectroscopic methods such as infrared spectroscopy. In some embodiments, the surfactant is at least partially removed from the nanofibres, for example, at least about 50% of the surfactant is removed from the nanofibres. In other embodiments, the surfactant is not substantially removed (e.g., less than about 50% is removed) from the nanofibres.

In various embodiments, antibacterial nanofibres are derived from nanofibres having an average diameter from about 50 nm to about 500 nm, from about 60 nm to about 400 nm, from about 70 nm to about 300 nm, from about 70 nm to about 200 nm, from about 80 nm to about 200 nm, from about 90 nm to about 150 nm, or from about 100 nm to about 140 nm. In embodiments, the average fibre diameter is less than about 200 nm, less than about 150 nm, or less than about 130 nm. In some embodiments, the average fibre diameter is greater than about 50 nm, greater than about 70 nm, or greater than about 90 nm.

In various embodiments, nanofibres described herein form nanofibrous structures, for example, nanofibrous mats. In some embodiments, the nanofibres comprise as-spun biopolymers. In exemplary embodiments, the nanofibres and/or nanofibrous mats are chemically treated with an antibacterial agent to generate antibacterial nanofibres. As described herein, at least in some implementations, nanofibres are inclusive of nanofibres within a nanofibrous structure.

In some embodiments, the antibacterial nanofibres or nanofibrous structures provided herein comprise one or more components useful for wound treatment. In some embodiments, a wound dressing comprising antibacterial nanofibres comprises one or more components useful for wound treatment. Non-limiting examples of components useful for wound treatment include drugs, antimicrobial compounds, lipids, triglycerides, vitamins, minerals, enzymes to minimize the development of malodorous compounds, and growth factors. Antimicrobial compounds include antiseptics (e.g., acetic acid, chlorhexidine, silver, iodine, hydrogen peroxide, sodium hypochlorite, potassium permanganate, polyhexamethyl biguanide, triclosan) and antibiotics (e.g., gentamicin, ofloxacin, minocycline, tetracycline, metronidazole and derivatives thereof). Non-limiting examples of growth factors include epithelial growth factor, platelet derived growth factor, and human growth hormone. Non-limiting examples of vitamins include vitamin A, vitamin C and vitamin E. Non-limiting examples of minerals include copper and zinc.

Nanofibres are often water soluble and therefore unable to sustain in aqueous environments of biomedical applications, such as wound dressings. One method to convert soluble biopolymer nanofibres to insoluble nanofibres involves complexing the biopolymer with calcium (II) ions to generate calcium-biopolymer nanofibres. Calcium-biopolymer nanofibres may be formed by ion-exchange between calcium and a cation (e.g., sodium) in a cation-biopolymer complex (e.g., sodium-biopolymer complex). In some embodiments, an ion-exchange reaction is facilitated by soaking biopolymer nanofibres in a calcium treatment solution comprising calcium (II) ions (e.g., calcium (II) ions from calcium salts). In some embodiments, the biopolymer comprises alginate or alginate salts such as sodium alginate. Exemplary calcium salts include, without limitation, calcium chloride, calcium bromide, calcium fluoride, calcium iodide, calcium nitrate, calcium hydride, calcium sulfate, calcium phosphate, calcium oxalate, calcium nitrite, calcium molybdate, calcium benzoate and calcium carbonate. The percentage of calcium (II) ions or calcium salts in the calcium treatment solution, in many embodiments, is from about 0.1% to about 10%, from about 0.1% to about 9%, from about 0.1% to about 8%, from about 0.1% to about 7%, from about 0.1% to about 6%, from about 0.1% to about 5%, from about 0.5% to about 10%, from about 0.5% to about 9%, from about 0.5% to about 8%, from about 0.5% to about 7%, from about 0.5% to about 6%, from about 0.5% to about 5%, or from about 1% to about 5%. In exemplary embodiments, the percentage of calcium (II) ions or calcium salts in the calcium treatment solution is about 0.5%, about 1%, about 1.5%, about 2%, about 2.5%, about 3%, about 3.5%, about 4%, about 4.5, or about 5%. Nanofibres may be treated with a calcium treatment solution for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 12 minutes, at least about 15 minutes, or at least about 20 minutes. In some instances, nanofibres are treated with a calcium treatment solution for less than about 30 minutes, less than about 25 minutes, less than about 20 minutes, less than about 15 minutes, or less than about 10 minutes. In one example, nanofibres are treated with a calcium treatment solution for 5 minutes, 6 minutes, 7 minutes, 8 minutes, 9 minutes, 10 minutes, 11 minutes, 12 minutes, 13 minutes, 14 minutes, or 15 minutes.

In some embodiments, nanofibre insolubility is maintained by dissolving the calcium (II) ions in an organic solvent or an organic miscible solvent to produce the calcium treatment solution. Organic solvents or organic miscible solvents include, without limitation, ethanol, acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol dimethyl ether), 1,2-dimethoxy-ethane (glyme, DME), dimethyl-formamide (DMF), dimethyl sulfoxide (DMSO), 1,4-dioxane, ethyl acetate, ethylene glycol, glycerin, heptane, Hexamethylphosphoramide (HMPA), Hexamethylphosphorous triamide (HMPT), hexane, methanol, methyl t-butyl ether (MTBE), methylene chloride, N-methyl-2-pyrrolidinone (NMP), nitromethane, pentane, 1-propanol, 2-propanol, tetrahydrofuran (THF), toluene, triethyl amine, heavy water, and any solutions (e.g., 50% organic solvent, 90% organic solvent) or combinations thereof. In one example, the calcium treatment solution comprises calcium (II) ions (e.g., calcium (II) ions from $CaCl_2$) dissolved in ethanol (e.g., ethanol absolute or >98% ethanol).

Antibacterial Nanofibres

The nanofibres described herein are receptive to complexing or retaining antimicrobial agents, e.g., antimicrobials such as silver. In some embodiments, nanofibres, such as as-spun nanofibres comprising a biopolymer, are chemically treated with an antibacterial treatment solution to generate antibacterial nanofibres. In some embodiments, the nanofibres for antibacterial treatment are produced by electrospinning a solution comprising a biopolymer and optionally one or more carrier polymers and/or surfactants. In some embodiments, the nanofibres are washed prior to antibacterial treatment. In some embodiments, the nanofibres are washed with a solution comprising an organic solvent, for example, ethanol. In some embodiments, the nanofibres are treated with a solution to render the nanofibres insoluble prior to antibacterial treatment. In some examples, the biopolymer comprises alginate. In some examples, the antibacterial treatment solution comprises silver. In some examples, the solution rendering the nanofibres insoluble comprises calcium (II) ions.

In some instances, nanofibres for antibacterial chemical treatment are nanofibres or nanofibrous mats in a wound dressing or a dressing structure. A dressing structure includes any structural component of a wound dressing, for example, a nanofibrous mat, a backing, an absorptive layer, and any combination thereof. A nanofibrous structure or nanofibre structure, in many instances, includes a nanofibrous mat. In other instances, a nanofibrous structure of nanofibre structure comprises nanofibres (including, in some cases, a nanofibrous mat) and a structural support, e.g., a backing.

In various embodiments, nanofibres are chemically treated, e.g., by soaking, with a silver treatment solution comprising silver (I) ions, resulting in nanofibres incorporated with silver. In some embodiments, during silver treatment, silver (I) ions are ion-exchanged with cations complexed to the biopolymers of the nanofibres to generate silver-biopolymer complexes. In exemplary embodiments, silver (I) ions are ion-exchanged with cations in cation-alginate nanofibres to generate cation-alginate complexes, wherein the cations are optionally sodium (I) ions. In some embodiments, silver (I) ions are ion-exchanged with calcium (II) ions in calcium-alginate nanofibres to generate silver-alginate complexes. In some instances, silver (I) ions are complexed with calcium-alginate nanofibres to generate silver-alginate-calcium complexes. In some embodiments, silver (I) ions from the silver treatment solution are precipitated as particles within nanofibres, for example, by the generation of insoluble silver salts (e.g., silver chloride). In exemplary embodiments, nanofibres are sequentially treated with a calcium solution and a silver treatment solution. In some embodiments, nanofibres are washed with a solution (e.g., organic solvent) suitable for removing one or more non-biopolymer components (e.g., carriers, surfactants) in the nanofibres prior to chemical treatment with a calcium solution, silver solution or both calcium and silver solutions. Nanofibres incorporated with silver (I) ions are antibacterial nanofibres, at least in some instances.

In some embodiments, a silver treatment solution comprises a silver salt including, but not limited to silver nitrate, silver chloride, silver sulfate, silver lactate, silver bromide, silver acetate, any silver salt miscible or soluble in an organic solvent, and any combination thereof.

In some embodiments, the silver treatment solution comprises from about 0.1% to about 5%, from about 0.1% to about 4%, from about 0.1% to about 3%, from about 0.1% to about 2%, from about 0.2% to about 5%, from about 0.2% to about 4%, from about 0.2% to about 3%, from about 0.2% to about 2%, from about 0.3% to about 2%, from about 0.4% to about 2%, or from about 0.5% to about 1% silver (I) ions. In exemplary embodiments, the percentage of silver (I) ions in the silver treatment solution is about 0.5%, about 1%, about 1.5%, about 2%, about 2.5%, about 3%, about 3.5%, about 4%, about 4.5%, or about 5%. The silver treatment solution is preferably a solution of silver (I) ions dissolved in a solution that maintains the structural integrity of the nanofibres, i.e., does not dissolve the nanofibres within a reasonable period of time, e.g., 24 hours. In one example, the silver treatment solution comprises silver (I) ions dissolved in a solution comprising an organic solvent, such as ethanol. Nanofibres may be treated with a silver treatment solution for at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 12 minutes, at least about 15 minutes, or at least about 20 minutes. In some instances, nanofibres are treated with a silver treatment solution for less than about 30 minutes, less than about 25 minutes, less than about 20 minutes, less than about 15 minutes, or less than about 10 minutes. In one example, nanofibres are treated with a silver treatment solution for 5 minutes, 6 minutes, 7 minutes, 8 minutes, 9 minutes, 10 minutes, 11 minutes, 12 minutes, 13 minutes, 14 minutes, or 15 minutes.

Properties of Antibacterial Nanofibres

In various aspects, provided herein are antibacterial nanofibres suitable for use in a wound dressing, wherein the antibacterial nanofibres are prepared by chemically treating biopolymer nanofibres. In various instances, the antibacterial nanofibres are prepared from as-spun nanofibres comprising a biopolymer and optionally a carrier and/or surfactant. In exemplary embodiments, the as-spun nanofibres comprise alginate, and optionally PEO and/or Triton™ X-100. In some embodiments, the as-spun nanofibres are treated with antimicrobial ions, for example, with a silver treatment solution, to generate the antibacterial nanofibres. In some embodiments, the as-spun nanofibres are treated with a solution configured to render the nanofibres insoluble in aqueous solution. In some embodiments, the as-spun nanofibres are treated with a calcium treatment solution prior to treatment with antimicrobial ions. The chemical composition of the antibacterial nanofibres, as well as its properties for functioning in a wound dressing (e.g., absorptivity, antimicrobial content, structural stability) are dependent, in whole or in part, on the identities and concentrations of nanofibre components prior to and after one or more treatments, as well as the identities and concentrations of reactive agents in nanofibre treatment solutions (e.g., calcium treatment solution, silver treatment solution).

Chemically treated nanofibres, as used herein, refer to nanofibres treated with a solution for rendering the nanofibres insoluble, (e.g., calcium solution), an antimicrobial solution (e.g., silver solution), or a combination thereof The chemical composition of antibacterial nanofibres treated with silver is dependent, at least in part, on the percentage of silver (I) ions in the silver treatment solution. In some embodiments, silver (I) ions comprises from about 5% to about 75%, from about 10% to about 75%, from about 15% to about 75%, from about 20% to about 75%, from about 25% to about 75%, from about 30% to about 75%, from about 35% to about 75%, from about 40% to about 75%, from about 45% to about 75%, from about 50% to about 75%, from about 50% to about 70%, or from about 50% to about 65% of the weight of the antibacterial nanofibres that is not attributed to elemental carbon. In some examples, the percentage of silver (I) in the treated antibacterial nanofibres is less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 1% of the weight of the antibacterial nanofibres not attributed to elemental carbon. In other or additional examples, the percentage of silver (I) in the treated antibacterial nanofibres is greater than about 0.1%, greater than about 0.5%, greater than about 1%, greater than about 2%, greater than about 3%, greater than about 4%, greater than about 5%, greater than about 6%, greater than about 7%, greater than about 8%, greater than about 9%, greater than about 10%, greater than about 15%, greater than about 20%, greater than about 25%, or greater than about 50% of the weight of the antibacterial nanofibres not attributed to elemental carbon.

In various embodiments, silver (I) ions in antibacterial nanofibres are complexed with biopolymers (e.g., alginate), precipitated with anionic salts (e.g., chloride), or a combination thereof. In some embodiments, the silver (I) ions in the antibacterial nanofibres are released by ion exchange in an aqueous environment comprising salts, for example, a wound. In some examples, silver (I) ions exchanged into the aqueous environment are silver (I) ions that were complexed with biopolymers (e.g., alginate) in the nanofibres.

The chemical composition of antibacterial nanofibres that have been treated with calcium is dependent, at least in part, on the percentage of calcium (II) ions in the calcium treatment solution. In some embodiments, the percentage of calcium (II) in the treated antibacterial nanofibres is from about 1% to about 50%, from about 2% to about 20%, preferably less than about 20%, more preferably less than about 15% of the weight of the antibacterial nanofibres not attributed to elemental carbon.

In some embodiments, calcium in the antibacterial nanofibres, upon contact with a wound, is ion-exchanged with sodium ions in the wound to act as a hemostatic agent for facilitating wound healing. In some examples, a nanofibre comprising calcium-alginate participates in an ion-exchange with sodium in a wound to generate a sodium alginate gel. This sodium alginate gel is useful for maintaining a moist healing microenvironment for the wound.

In some embodiments, the percentage of oxygen in the treated antibacterial nanofibres is from about 5% to about 50%, preferably from about 10% to about 25%, or more preferably from about 15% to about 25% of the weight of the antibacterial nanofibres not attributed to elemental carbon.

In some embodiments, the antibacterial nanofibres have been treated with a solution of calcium chloride. In these instances, the concentration of chloride in the treated nanofibres is from about 1% to about 25% or is less than 1%. In some embodiments, the concentration of chloride in the treated antibacterial nanofibres is from about 1% to about 20%, from about 3% to about 20%, from about 5% to about 20%, from about 1% to about 10%, from about 2% to about 10%, from about 3% to about 10%, or from about 5% to about 10%. In some embodiments, the concentration of chloride in the treated antibacterial nanofibres is less than about 20%, less than about 15%, less than about 10%, less than about 9%, less than about 8%, less than about 7%, less than about 6%, or less than about 5%. In exemplary embodiments, the concentration of chloride in the treated antibacterial nanofibres is between 1% and 10% of the weight of the antibacterial nanofibres not attributed to elemental carbon.

In some embodiments, the antibacterial nanofibres are derived from chemically treated sodium-alginate nanofibres. In some embodiments, the concentration of sodium in the treated nanofibres is from about 1% to about 20% or is less than 1% of the weight of the antibacterial nanofibres not attributed to elemental carbon. In some embodiments, the concentration of sodium in the treated nanofibres is from about 1% to about 15%, from about 1% to about 10%, from about 1% to about 9%, from about 1% to about 8%, from about 1% to about 7%, from about 1% to about 6%, from about 1% to about 5%, from about 2% to about 10%, or from about 2% to about 5% of the weight of the antibacterial nanofibres not attributed to elemental carbon. In some embodiments, the concentration of sodium in the treated nanofibres is less than about 10%, less than about 9%, less than about 8%, less than about 7%, less than about 6%, or less than about 5%. In exemplary embodiments, the concentration of sodium in the treated nanofibres is between 1% and 5% of the weight of the antibacterial nanofibres not attributed to elemental carbon.

In some embodiments, the antibacterial nanofibres are derived from as-spun nanofibres prepared by electrospinning a solution comprising a biopolymer and a carrier polymer. In some embodiments, the carrier polymer is PEO. In many instances, the antibacterial nanofibres do not comprise detectable traces of carrier polymer. For example, the carrier polymer is not detected in a nanofibre by spectroscopic techniques such as infrared spectroscopy. In some embodiments, at least 90%, at least 95%, or at least 99% of the carrier polymer is not present in the antibacterial nanofibres.

In various embodiments, the morphology of the nanofibres changes after chemical treatment. For example, the average fibre diameters decrease or increase depending on the type of chemical treatment. In some examples, sequential treatment with calcium and silver solutions results in antibacterial nanofibres having smaller average fibre diameters than the nanofibres from which they were derived. In some embodiments, chemical treatment results in nanofibres having between a 1% and a 50% decrease in average fibre diameter. In some embodiments, the decrease in average fibre diameter is between about 1% and about 20%, between about 1% and about 10%, between about 1% and about 9%, between about 1% and about 8%, between about 2% and about 10%, between about 2% and about 9%, between about 2% and about 8%, or between about 3% and about 8%. In some embodiments, the decrease in average fibre diameter is less than about 10%, less than about 9%, less than about 8%, less than about 7%, less than about 6%, less than about 5%, less than about 4%, less than about 3%, less than about 2%, or less than about 1%. In some embodiments, the average fibre diameter does not substantially decrease after chemical treatment. In some embodiments, the average fibre diameter increases after chemical treatment. In some embodiments, the average fibre diameter of chemically treated antibacterial nanofibres is from about 30 nm to about 500 nm, from about 60 nm to about 440 nm, from about 80 nm to about 200 nm, from about 100 nm to about 160 nm, from about 110 nm to about 150, from about 120 nm to about 150 nm, from about 125 nm to about 145 nm, or from about 125 nm to about 140 nm. In some embodiments, the antibacterial nanofibres were derived from sodium-alginate nanofibres, wherein the sodium-alginate nanofibres where optionally produced by electrospinning a solution comprising sodium alginate and PEO.

In some instances, treatment of nanofibres with an antibacterial agent results in antibacterial nanofibres having a wider fibre diameter distribution than nanofibres prior to treatment. In some embodiments, the nanofibres were sequentially treated with calcium and silver solutions. In some embodiments, at least about 75% of antibacterial nanofibres have fibre diameters between about 80 nm and about 200 nm, or between about 80 nm and about 160 nm. In some embodiments, at least about 50% of antibacterial nanofibres have fibre diameters between about 80 nm and 160 nm or between about 100 nm and about 140 nm.

In some instances, treatment of nanofibres with an antibacterial agent results in breakage of one or more nanofibres in a nanofibre structure. In some embodiments, the nanofibres were sequentially treated with calcium and silver solutions. In some embodiments, nanofibre breakage is correlated, at least in part, to the concentration of calcium (II) ions in a calcium treatment solution. For example, a nanofibre structure treated with a 5% solution of $CaCl_2$ has more broken nanofibres than a nanofibre structure treated with 1-4% solution of $CaCl_2$), e.g., a 1% solution of $CaCl_2$).

In some instances, treatment of nanofibres in a nanofibre structure with an antibacterial agent results in an antibacterial nanofibre structure comprising a plurality of spherical particles. In some embodiments, the nanofibres were sequentially treated with calcium and silver solutions. In some embodiments, the spherical particles comprise elemental silver and/or silver (I) ions, wherein the silver (I) ions are optionally precipitated, for example, with chloride or another anionic salt during the treatment process. In some embodiments, the spherical particles have diameters from about 100 nm to about 350 nm or from about 150 nm to about 300 nm. In another embodiment, the average diameter of spherical particles is from about 180 nm to about 250 nm, from about 190 nm to about 230 nm, or from about 200 nm to about 220 nm, wherein the standard deviation is from about 10 nm to about 50 nm.

In some instances, treatment of nanofibres with an antibacterial agent results in antibacterial nanofibres having increased resistance to solubility in aqueous environments as compared to the nanofibres from which they were derived. In some embodiments, the nanofibres were sequentially treated with calcium and silver solutions. For example, the antibacterial nanofibres remain intact after solubility tests are performed in accordance with BS EN 13726-1:2002 section 3.7 dispersion and solubility of hydrogel dressings in water. In some embodiments, antibacterial nanofibres soaked in water or a simulated test solution (STS) remain insoluble for at least 120 minutes at room temperature (e.g., between about 20° C. and 25° C.). In some embodiments, antibacterial nanofibres soaked in water remain insoluble for at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 24 hours, or at least 48 hours. Insolubility of the soaked antibacterial nanofibres may be assessed by visual inspection. An exemplary STS is an aqueous solution comprising serum and one or more salts to mimic wound exudate. In one example, STS comprises 0.4 M sodium chloride, 0.02 M calcium chloride and 10% newborn calf serum.

Nanofibre Compositions

In various aspects, provided herein are antibacterial nanofibres suitable for use in a wound dressing, wherein the antibacterial nanofibres are prepared by chemically treating biopolymer nanofibres. In various instances, the antibacterial nanofibres are prepared from as-spun nanofibres comprising a biopolymer and optionally a carrier and/or surfactant. In some embodiments, the biopolymer comprises alginate. In some embodiments, the carrier comprises PEO. In some embodiments, the surfactant is Triton™ X-100. The nanofibres, e.g., as-spun nanofibres, are treated with antimicrobial ions, for example, with a silver treatment solution, to generate the antibacterial nanofibres. In some embodiments, the nanofibres are treated with a solution configured to render the nanofibres insoluble in aqueous solution. In some embodiments, the as-spun nanofibres are treated with a calcium treatment solution prior to treatment with antimicrobial ions.

The antibacterial nanofibres provided herein, in various embodiments, are combined with one or more elements of a wound dressing and/or are further treated with one or more agents useful in a wound dressing. In some embodiments, an agent useful in a wound dressing is a malodor absorbing agent, such as cyclodextrin.

In some embodiments, nanofibres are combined with a backing to form a composite dressing structure or nanofibrous dressing structure. In some embodiments, the nanofibres are antibacterial nanofibres. In some embodiments, the nanofibres are combined with a backing and then chemically treated to generate antibacterial nanofibres within a nanofibrous dressing structure. The composite dressing structure is suitable for use as a wound dressing or as a component of a wound dressing. A suitable backing is a mechanically stable material useful for constructing a wound dressing. A suitable backing includes, without limitation, a nonwoven backing comprising, for example, carboxymethylcellulose (CMC). In some embodiments, nanofibres are electrospun onto a backing. In some embodiments, nanofibres or nanofibre structures are attached to a backing. In some embodiments, nanofibres are disposed between a backing and another wound dressing component or layer. In various cases, the nanofibres are alginate nanofibres, for example, as-spun alginate nanofibres. In some embodiments, the backing is useful for absorbing wound exudates, providing a barrier from bacterial penetration and foreign contamination, allowing oxygen balance in the wound, assisting in cell growth, or any combination thereof.

In various embodiments, nanofibrous dressing structures are chemically treated to generate insoluble nanofibres (e.g., calcium treatment). In some embodiments, nanofibrous dressing structures are chemically treated to generate antibacterial nanofibres (e.g., silver treatment). In some embodiments, a nanofibrous dressing structure is chemically treated with sequential solutions of calcium and silver. In some embodiments, nanofibres are chemically treated with sequential solutions of calcium and silver and then deposited, attached, or otherwise combined with a backing to generate an antibacterial nanofibrous dressing structure. In some examples, the nanofibrous dressing structures comprise nanofibres and a backing. In some examples, the nanofibres are alginate nanofibres, for example, as-spun alginate nanofibres.

In various embodiments, an antibacterial nanofibrous dressing structure is prepared by a) depositing a biopolymer solution onto a backing to generate a nanofibrous structure, b) contacting the nanofibrous structure with a calcium solution to generate calcium-biopolymer nanofibres, and c) contacting the calcium-biopolymer nanofibres with a silver solution to generate an antibacterial nanofibrous dressing structure comprising silver-biopolymer nanofibres. In some instances, the biopolymer solution is deposited onto the backing by electrospinning. In some instances, the biopolymer solution is electrospun to form as-spun nanofibres. In some instances, the biopolymer solution comprises a biopolymer and optionally a carrier and/or surfactant. In some examples, the biopolymer comprises alginate. In some cases, the carrier is PEO. In some cases, the surfactant is Triton™ X-100. In some embodiments, the nanofibrous structure is washed with an organic solvent prior to contacting with the calcium solution. In some embodiments, the calcium solution comprises calcium (II) ions dissolved in an organic solvent, e.g., ethanol. In some embodiments, the silver solution comprises silver (I) ions dissolved in an organic solvent, e.g., ethanol. In various implementations, the method further comprises contacting the antibacterial nanofibrous dressing structure with an organic solvent to remove precipitated and unreacted salts. In some implementations, the method further comprises drying the antibacterial nanofibrous dressing structure. In some embodiments, the backing comprises CMC. In various implementations, the antibacterial nanofibrous dressing structure is combined with one or more additional wound dressing components and or wound dressing additives to generate a wound dressing.

In some embodiments, an antibacterial nanofibrous dressing structure is prepared by a) combining nanofibres with a backing to generate a nanofibrous structure, b) contacting the nanofibrous structure with a calcium solution to generate calcium-complexed nanofibres, and c) contacting the calcium-complexed nanofibres with a silver solution to generate an antibacterial nanofibrous dressing structure comprising silver-complexed nanofibres. In some embodiments, the nanofibres are as-spun nanofibres. In some embodiments, the nanofibres comprise a biopolymer and optionally a carrier and/or surfactant. In some embodiments, the nanofibres are as-spun from a solution comprising a biopolymer and optionally a carrier and/or surfactant. In some examples, the biopolymer comprises alginate. In some cases, the carrier is PEO. In some cases, the surfactant is Triton™ X-100. In some embodiments, the nanofibrous structure is washed with an organic solvent prior to contacting with the calcium solution. In some embodiments, the calcium solution comprises calcium (II) ions dissolved in an organic solvent, e.g., ethanol. In some embodiments, the silver solution comprises silver (I) ions dissolved in an organic solvent, e.g., ethanol. In various implementations, the method further comprises contacting the antibacterial nanofibrous dressing structure with an organic solvent to remove precipitated and unreacted salts. In some implementations, the method further comprises drying the antibacterial nanofibrous dressing structure. In some embodiments, the backing comprises CMC. In various implementations, the antibacterial nanofibrous dressing structure is combined with one or more additional wound dressing components and or wound dressing additives to generate a wound dressing.

In some embodiments, an antibacterial nanofibrous dressing structure is prepared by a) chemically treating nanofibres with an antibacterial agent to generate antibacterial nanofibres and b) combining the antibacterial nanofibres with a backing. In some cases, the nanofibres are chemically treated by i) application of a solution rendering the nanofibres insoluble and ii) application of a solution comprising an antibacterial agent. In some embodiments, the antibacterial agent is silver. In some embodiments, the backing comprises CMC. In various implementations, the antibacterial nanofibrous dressing structure is combined with one or more additional wound dressing components and or wound dressing additives to generate a wound dressing.

In some embodiments, a nanofibrous structure described herein is treated with a calcium solution. In some embodiments, a nanofibrous structure comprises a backing comprising CMC. In some examples, a nanofibrous structure comprising CMC has been treated with a calcium solution, resulting in calcium-CMC complexes. In some embodiments, a nanofibrous structure comprises alginate nanofibres, wherein treatment of the nanofibres (prior to after combining with a backing) with a calcium solution results in calcium-alginate complexes. In some instances, calcium-CMC complexes and/or calcium-alginate complexes occur through ion-exchange. These ion-exchange reactions may be equilibrium reactions, with a constant flux of ion exchange.

In some embodiments, a nanofibrous structure described herein is treated with a silver solution. In some embodiments, a nanofibrous structure comprises a backing comprising CMC. In some examples, a nanofibrous structure comprising CMC has been treated with a silver solution, resulting in silver-CMC complexes. In some embodiments, a nanofibrous structure comprises alginate nanofibres, wherein treatment of the nanofibres (prior to or after combining with a backing) with a silver solution results in silver-alginate complexes. In some instances, silver-CMC complexes and/or silver-alginate complexes occur through ion-exchange. These ion-exchange reactions may be equilibrium reactions, with a constant flux of ion exchange.

In various embodiments, nanofibres (including nanofibrous mats, nanofibres in nanofibrous structures, nanofibres in a wound dressing or wound dressing component) are combined with or coated with a malodor absorbing agent to generate nanofibres having malodor absorption properties. In some cases, the nanofibres are antibacterial nanofibres. In some cases, the nanofibres are combined or coated with a malodor absorbing agent and then treated to generate antibacterial nanofibres having malodor absorption properties. Malodorous nanofibres are useful as a component in a nanofibrous wound dressing. Exemplary malodor absorbing agents include cyclodextrins. In some embodiments, the malodor absorbing agent is electrospun onto the nanofibres. In some embodiments, the malodor absorbing agent is electrosprayed onto the nanofibres. In some embodiments, the malodor absorbing agent is attached to or placed next to the nanofibres, for example, as layers in a wound dressing.

An exemplary malodor absorbing agent comprises a cyclodextrin. Cyclodextrins include α-, β-, γ-cyclodextrins and combinations thereof. In some embodiments, the malodor absorbing agent is hydroxypropyl-β-cyclodextrin (HP-β-CD).

In various embodiments, an anti-odor, antibacterial nanofibrous dressing structure is prepared by a) depositing a biopolymer solution onto a backing to generate a nanofibrous structure, b) contacting the nanofibrous structure with a calcium solution to generate calcium-biopolymer nanofibres, c) contacting the calcium-biopolymer nanofibres with a silver solution to generate an antibacterial nanofibrous structure comprising silver-biopolymer nanofibres, and d) depositing a malodor absorbing agent onto a surface of the antibacterial nanofibrous structure to generate an anti-odor, antibacterial nanofibrous dressing structure. In some instances, the biopolymer solution is deposited onto the backing by electrospinning. In some instances, the biopolymer solution is electrospun to form as-spun nanofibres. In some instances, the biopolymer solution comprises a biopolymer and optionally a carrier and/or surfactant. In some examples, the biopolymer comprises alginate. In some cases, the carrier is PEO. In some cases, the surfactant is Triton™ X-100. In some embodiments, the nanofibrous structure is washed with an organic solvent prior to contacting with the calcium solution. In some embodiments, the calcium solution comprises calcium (II) ions dissolved in an organic solvent, e.g., ethanol. In some embodiments, the silver solution comprises silver (I) ions dissolved in an organic solvent, e.g., ethanol. In various implementations, the method further comprises contacting the antibacterial nanofibrous dressing structure with an organic solvent to remove precipitated and unreacted salts. In some implementations, the method further comprises drying the antibacterial nanofibrous dressing structure. In some embodiments, the backing comprises CMC. In some instances, the malodor absorbing agent is deposited onto the antibacterial nanofibrous structure by electrospinning. In some instances, the malodor absorbing agent is deposited onto the antibacterial nanofibrous structure by electrospraying. In some examples, the malodor absorbing agent is a cyclodextrin, such as HP-β-CD. In various implementations, the anti-odor, antibacterial nanofibrous dressing structure is combined with one or more additional wound dressing components and or wound dressing additives to generate a wound dressing.

In some embodiments, an anti-odor, antibacterial nanofibrous dressing structure is prepared by a) combining nanofibres with a backing to generate a nanofibrous structure, b) contacting the nanofibrous structure with a calcium solution to generate calcium-complexed nanofibres, c) contacting the calcium-complexed nanofibres with a silver solution to generate an antibacterial nanofibrous structure comprising silver-complexed nanofibres, and d) depositing a malodor absorbing agent onto a surface of the antibacterial nanofibrous structure to generate an anti-odor, antibacterial nanofibrous dressing structure. In some embodiments, the nanofibres are as-spun nanofibres. In some embodiments, the nanofibres comprise a biopolymer and optionally a carrier and/or surfactant. In some embodiments, the nanofibres are as-spun from a solution comprising a biopolymer and optionally a carrier and/or surfactant. In some examples, the biopolymer comprises alginate. In some cases, the carrier is PEO. In some cases the surfactant is Triton™ X-100. In some embodiments, the nanofibrous structure is washed with an organic solvent prior to contacting with the calcium solution. In some embodiments, the calcium solution comprises calcium (II) ions dissolved in an organic solvent, e.g., ethanol. In some embodiments, the silver solution comprises silver (I) ions dissolved in an organic solvent, e.g., ethanol. In various implementations, the method further comprises contacting the antibacterial nanofibrous dressing structure with an organic solvent to remove precipitated and unreacted salts. In some implementations, the method further comprises drying the antibacterial nanofibrous dressing structure. In some embodiments, the backing comprises CMC. In some instances, the malodor absorbing agent is deposited onto the antibacterial nanofibrous structure by electrospinning. In some instances, the malodor absorbing agent is deposited onto the antibacterial nanofibrous structure by electrospraying. In some examples, the malodor absorbing agent is a cyclodextrin, such as HP-β-CD. In various implementations, the anti-odor, antibacterial nanofibrous dressing structure is combined with one or more additional wound dressing components and or wound dressing additives to generate a wound dressing.

In some embodiments, an anti-odor, antibacterial nanofibrous dressing structure is prepared by a) chemically treating nanofibres with an antibacterial agent to generate antibacterial nanofibres, b) combining the antibacterial nanofibres with a backing to generate an antibacterial nanofibrous structure, and c) depositing a malodor absorbing agent onto a surface of the antibacterial nanofibrous structure to generate an anti-odor, antibacterial nanofibrous dressing structure. In some cases, the nanofibres are chemically treated by i) application of a solution rendering the nanofibres insoluble and ii) application of a solution comprising an antibacterial agent. In some embodiments, the antibacterial agent is silver. In some embodiments, the backing comprises CMC. In some instances, the malodor absorbing agent is deposited onto the antibacterial nanofibrous structure by electrospinning. In some instances, the malodor absorbing agent is deposited onto the antibacterial nanofibrous structure by electrospraying. In some examples, the malodor absorbing agent is a cyclodextrin, such as HP-β-CD. In various implementations, the anti-odor, antibacterial nanofibrous dressing structure is combined with one or more additional wound dressing components and or wound dressing additives to generate a wound dressing.

In some embodiments, an anti-odor, antibacterial nanofibrous dressing structure is prepared by a) chemically treating nanofibres with an antibacterial agent to generate antibacterial nanofibres, b) depositing a malodor absorbing agent onto a surface of the antibacterial nanofibres to generate anti-odor antibacterial nanofibres, and c) combining the anti-odor antibacterial nanofibres with a backing to generate an anti-odor, antibacterial nanofibrous dressing structure. In some cases, the nanofibres are chemically treated by i) application of a solution rendering the nanofibres insoluble and ii) application of a solution comprising an antibacterial agent. In some embodiments, the antibacterial agent is silver. In some embodiments, the backing comprises CMC. In some instances, the malodor absorbing agent is deposited onto the antibacterial nanofibres by electrospinning. In some instances, the malodor absorbing agent is deposited onto the antibacterial nanofibres by electrospraying. In some examples, the malodor absorbing agent is a cyclodextrin, such as HP-β-CD. In various implementations, the anti-odor, antibacterial nanofibrous dressing structure is combined with one or more additional wound dressing components and or wound dressing additives to generate a wound dressing.

In some embodiments, nanofibres are electrosprayed with a solution comprising a malodor absorbing agent. These nanofibres include, without limitation, nanofibrous mats, nanofibres in nanofibrous structures and nanofibres in a wound dressing or a wound dressing component. Nanofibrous structures include, without limitation, nanofibrous structures comprising nanofibres and a backing (e.g., a CMC comprising backing). These nanofibres also include antibacterial nanofibres described herein (e.g., silver treated nanofibres). In some embodiments, the nanofibres comprise alginate. In some embodiments, the malodor absorbing agent is HP-β-CD. The solution comprising a malodor absorbing agent (e.g., HP-β-CD) may comprise between about 1% and about 90%, between about 5% and about 80%, between about 10% and about 80%, between about 20% and about 80%, between about 20% and about 70%, between about 30% and 80%, between about 30% and 70%, between about 20% and about 60%, between about 20% and about 50%, between about 30% and about 60%, between about 30% and about 50%, or between about 35% to about 45% by weight malodor absorbing agent. In one example, the solution comprising a malodor absorbing agent (e.g., HP-β-CD) comprises 40% by weight malodor absorbing agent. Solution feed rates for electrospraying a solution comprising a malodor absorbing agent (e.g., HP-β-CD) onto nanofibres include, in at least in some embodiments, feed rates between about 0.1 ml/hour to about 5 ml/hour, between about 0.2 ml/hour to about 5 ml/hour, between about 0.3 ml/hour to about 5 ml/hour, between about 0.2 ml/hour to about 4 ml/hour, between about 0.3 ml/hour to about 4 ml/hour, between about 0.3 ml/hour to about 3 ml/hour, between about 0.3 ml/hour to about 2 ml/hour, between about 0.4 ml/hour to about 5 ml/hour, between about 0.4 ml/hour to about 4 ml/hour, between about 0.4 ml/hour to about 3 ml/hour, between about 0.4 ml/hour to about 2 ml/hour, between about 0.5 ml/hour to about 5 ml/hour, between about 0.5 ml/hour to about 4 ml/hour, between about 0.5 ml/hour to about 3 ml/hour, between about 0.5 ml/hour to about 2 ml/hour, between about 0.8 ml/hour to about 1.5 ml/hour, or between about 0.8 ml/hour to about 1.2 ml/hour. In one example, the feed rate is about 1.0 ml/hour. A working distance for electrospraying a solution comprising a malodor absorbing agent (e.g., HP-β-CD) onto nanofibres include, in at least in some embodiments, a distance between about 10 cm and about 30 cm, between about 10 cm and about 25 cm, between about 10 cm and about 20 cm, between about 12 cm and about 20 cm, between about 10 cm and about 18 cm, between about 12 cm and about 18 cm. In one example, the working distance from the syringe of the electrospray device to the nanofibres is about 16 cm. In some embodiments, the solution comprising a malodor absorbing agent (e.g., HP-β-CD) is electrosprayed with an applied voltage between 2 kV and 30 kV, between 4 kV and 25 kV, between 4 kV and 20 kV, between 5 kV and 25 kV, between 5 kV and 20 kV, between 7 kV and 20 kV, or between 7 kV and 15 kV. In one example, a solution comprising a malodor absorbing agent (e.g., HP-β-CD) is electrosprayed with an applied voltage of about 12 kV. In some embodiments, the amount of a solution comprising a malodor absorbing agent (e.g., HP-β-CD) electrosprayed onto an antibacterial nanofibre structure having a size less than about 500 $cm^2$, less than about 400 $cm^2$, less than about 300 $cm^2$, less than about 200 $cm^2$, less than about 100 $cm^2$, or less than about 50 $cm^2$, is from about 0.5 ml to about 30 ml, from about 0.5 ml to about 25 ml, from about 0.5 ml to about 20 ml, from about 0.5 ml to about 15 ml, from about 0.5 ml to about 10 ml, from about 0.5 ml to about 8 ml, from about 0.5 ml to about 5 ml, or from about 1 ml to about 5 ml solution comprising a malodor absorbing agent. The time to electrospray a solution comprising a malodor absorbing agent (e.g., HP-β-CD) onto nanofibres may be from about 30 minutes to 6 hour, from about 1 hour to about 4 hour. In some embodiments, the electrospray time is 1 hour, 2 hours, or 4 hours. In some embodiments, the electrosprayed malodor absorbing agent (e.g., HP-β-CD) generates fibres. In some embodiments, the average malodorous fibre diameter depositing by electrospraying onto nanofibres is from about 300 nm to about 1,800 nm, from about 400 nm to about 1,600 nm, from about 500 nm to about 1,500 nm, from about 500 nm to about 1,200 nm, from about 500 nm to about 1,000 nm, from about 600 nm to about 1,000 nm, from about 600 nm to about 900 nm, or from about 700 nm to about 900 nm. In one example, the average electrosprayed malodor absorbing agent fibre diameter is about 850 nm.

In some embodiments, nanofibres are deposited with an electrospun solution comprising a malodor absorbing agent. These nanofibres include, without limitation, nanofibrous mats, nanofibres in nanofibrous structures and nanofibres in a wound dressing or a wound dressing component. Nanofibrous structures include, without limitation, nanofibrous structures comprising nanofibres and a backing (e.g., a CMC comprising backing). These nanofibres also include antibacterial nanofibres described herein (e.g., silver treated nanofibres). In some embodiments, the nanofibres comprise alginate. In some embodiments, the malodor absorbing agent is HP-β-CD. In some embodiments, the solution comprising a malodor absorbing agent (e.g., HP-β-CD) further comprises a carrier, for example, PEO. The solution comprising a malodor absorbing agent may comprise between about 1% and about 70%, between about 1% and about 60%, between about 1% and about 50%, between about 1% and about 40%, between about 1% and about 30%, between about 1% and 20%, between about 1% and 15%, between about 2% and about 15%, or between about 4% and about 12% by weight malodor absorbing agent. In some examples, the solution comprising a malodor absorbing agent comprises 40% by weight malodor absorbing agent. In some embodiments, the solution comprising a malodor absorbing agent comprises a malodor absorbing agent and a carrier. In some embodiments, the solution comprising a malodor absorbing agent has a malodor absorbing agent: carrier ratio of 30-95 agent to 70-5 carrier, 40-90 agent to 60-10 carrier, 50-90 agent to 50-10 carrier. In some embodiments, the agent:carrier ratio is 50:50, 60:40, 70:30, 80:20 or 90:10. Solution feed rates for electrospinning a solution comprising a malodor absorbing agent onto nanofibres include, in at least in some implementations, feed rates between about 0.1 ml/hour to about 5 ml/hour, between about between about between about between about between about between about between about 0.2 ml/hour to 0.2 ml/hour to 0.3 ml/hour to 0.4 ml/hour to 0.4 ml/hour to 0.5 ml/hour to 0.5 ml/hour to about 5 ml/hour, about 4 ml/hour, about 3 ml/hour, about 5 ml/hour, about 3 ml/hour, about 5 ml/hour, about 3 ml/hour between about 0.3 ml/hour to about 5 ml/hour, between about 0.3 ml/hour to about 4 ml/hour, between about 0.3 ml/hour to about 2 ml/hour, between about 0.4 ml/hour to about 4 ml/hour, between about 0.4 ml/hour to about 2 ml/hour, between about 0.5 ml/hour to about 4 ml/hour, between about 0.5 ml/hour to about 2 ml/hour, between about 0.8 ml/hour to about 1.5 ml/hour, or between about 0.8 ml/hour to about 1.2 ml/hour. In one example, the feed rate is about 1.0 ml/hour. A working distance for electrospinning a solution comprising a malodor absorbing agent onto nanofibres include, in at least in some implementations, a distance between about 10 cm and about 30 cm, between about 10 cm and about 25 cm, between about 10 cm and about 20 cm, between about 12 cm and about 20 cm, between about 10 cm and about 18 cm, between about 12 cm and about 18 cm. In one example, the working distance from the syringe of the electrospinning device to the nanofibres is about 12 cm. In some embodiments, the solution comprising a malodor absorbing agent is electrospun with an applied voltage between 2 kV and 30 kV, between 4 kV and 25 kV, between 4 kV and 20 kV, between 5 kV and 25 kV, between 5 kV and 20 kV, between 7 kV and 20 kV, or between 7 kV and 15 kV. In one example, the solution comprising a malodor absorbing agent is electrospun with an applied voltage of about 12 kV. In some embodiments, the amount of solution comprising a malodor absorbing agent electrospun onto a nanofibre structure having a size less than about 500 $cm^2$, less than about 400 $cm^2$, less than about 300 $cm^2$, less than about 200 $cm^2$, less than about 100 $cm^2$, or less than about 50 $cm^2$; is from about 0.5 ml to about 30 ml, from about 0.5 ml to about 25 ml, from about 0.5 ml to about 20 ml, from about 0.5 ml to about 15 ml, from about 0.5 ml to about 10 ml, from about 0.5 ml to about 8 ml, from about 0.5 ml to about 5 ml, or from about 1 ml to about 5 ml solution comprising a malodor absorbing agent. In some embodiments, the electrospun solution comprising a malodor absorbing agent (HP-β-CD) generates fibres. In some embodiments, the average malodor absorbing agent fibre diameter depositing by electrospinning onto nanofibres is from about 50 nm to about 1,800 nm, from about 50 nm to about 1,500 nm, from about 50 nm to about 1,000 nm, from about 50 nm to about 800 nm, from about 50 nm to about 700 nm, from about 50 nm to about 600 nm, from about 50 nm to about 500 nm, from about 50 nm to about 400 nm, from about 50 nm to about 300 nm, from about 100 nm to about 300 nm, or from about 150 nm to about 300 nm. In one example, the electrospun average malodor absorbing agent fibre diameter is about 200 nm, about 210 nm, about 220 nm, about 230 nm, about 240 nm, about 250 nm, about 260 nm, about 270 nm, about 280 nm, about 290 nm or about 300 nm.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

Example 1: Preparation and Characterization of Antibacterial Nanofibres Derived from Alginate Nanofibres Methods of preparing antibacterial nanofibres: Antibacterial nanofibre mats were prepared by chemical modification of as-spun sodium-alginate/PEO nanofibre mats. The as-spun nanofibres were generated by electrospinning an aqueous solution comprising 4% by weight sodium-alginate and PEO in a 70:30 ratio. The resulting as-spun nanofibres were bead free, as shown by Field Gun Emission Scanning Electron Microscopy (SEM) in FIG. 1, panel A1. As-spun sodium-alginate/PEO nanofibres were soaked in a petri-dish containing about 25 mL ethanol absolute. The petri-dish was gently shaken for 10 minutes while the PEO dissolved from the nanofibres. The soaked as-spun nanofibres were transferred to a second petri-dish comprising $CaCl_2$) in ethanol absolute for a second 10 minute soak. This second soak allowed for the exchange of sodium and calcium ions to generate calcium-alginate nanofibres. The calcium-alginate nanofibres were transferred to a third petri-dish comprising $AgNO_3$ in ethanol absolute for a third 10 minute soak. This third soak provided another ion exchange to generate silver-alginate nanofibres. The silver-alginate nanofibres were washed in ethanol absolute to remove precipitated and unreacted salts and subsequently dried at room temperature (20° C.). The concentrations of $CaCl_2$) and $AgNO_3$ used are shown in Table 1.

TABLE 1

Reaction conditions for four sets of chemically treated as-spun sodium-alginate/PEO nanofibres.

| Sample Nomenclature | Treated with $CaCl_2$ in ethanol absolute solution | | Treated with $AgNO_3$ in ethanol absolute solution | |
| --- | --- | --- | --- | --- |
| | $CaCl_2$ concentration | Treatment time | $AgNO_3$ concentration | Treatment time |
| T0.5/1.0Ag/Ca | 1.0% | 10 min | 0.5% | 10 min |
| T1.0/1.0Ag/Ca | 1.0% | 10 min | 1.0% | 10 min |

TABLE 1-continued

Reaction conditions for four sets of chemically treated as-spun sodium-alginate/PEO nanofibres.

| Sample Nomenclature | Treated with CaCl$_2$ in ethanol absolute solution | | Treated with AgNO$_3$ in ethanol absolute solution | |
|---|---|---|---|---|
| | CaCl$_2$ concentration | Treatment time | AgNO$_3$ concentration | Treatment time |
| T0.5/5.0Ag/Ca | 5.0% | 10 min | 0.5% | 10 min |
| T1.0/5.0Ag/Ca | 5.0% | 10 min | 1.0% | 10 min |

Characterization of antibacterial nanofibres: The morphology and characterization of antibacterial nanofibres were investigated by Field Gun Emission Scanning Electron Microscope (SEM) and Energy Dispersion X-ray (EDX) (Philips XL30 FEG-SEM) and Fourier Transform Infrared Spectroscopy (FTIR) (NICOLET5700 FT-IR, Thermo Electron Corporation).

Antibacterial nanofibre mats (0.5 cm×0.5 cm) were adhered on a specimen stub by carbon tape specific for SEM. The adhered mats were coated with carbon using gatan Precision Etching Coating System (model 682). SEM images were captured at 2,000×, 10,000×, 20,000× magnifications. SEM operating parameters were set at 6 kV accelerating voltage and a spot size of 3. Fibre diameters were manually measured using the line-drawing feature in ImageJ (ImageJ 2004) software from 50 randomly selected fibres in the 10,000× and 20,000× magnification images at 3 different focal points. For EDX analysis, scanning was performed at 2,000× magnification with 10 kV accelerating voltage and a spot size of 3.

SEM images showing nanofibre morphology before and after chemical treatment are provided in FIG. 1 (panels A1-E1). Corresponding fibre size distribution for each nanofibre mat is shown in FIG. 1 (panels A2-E2). FIG. 1, panel A1 is an image of as-spun sodium-alginate/PEO prior to chemical modification. FIG. 1, panel B1 is an image of a silver-alginate nanofibre mat after treatment with 1.0% CaCl$_2$) and 0.5% AgNO$_3$. FIG. 1, panel C1 is an image of a silver-alginate nanofibre mat after treatment with 1.0% CaCl$_2$) and 1.0% AgNO$_3$. FIG. 1, panel D1 is an image of a silver-alginate nanofibre mat after treatment with 5.0% CaCl$_2$) and 0.5% AgNO$_3$. FIG. 1, panel E1 is an image of a silver-alginate nanofibre mat after treatment with 5.0% CaCl$_2$) and 1.0% AgNO$_3$. The nanofibres prior to chemical treatment are more uniform in size than the nanofibres after chemical treatment. The structure of the T0.5/1.0/Ag/Ca and T1.0/1.0/Ag/Ca nanofibres are maintained after treatment, while the T0.05/5.0/Ag/Ca and T1.0/5.0/Ag/Ca have broken nanofibres.

As shown in FIG. 1 (panels A2-E2), the average diameter of the nanofibres decreased after chemical treatment and the fibre size distribution increased after chemical treatment. The average nanofibre diameter of the as-spun sodium-alginate/PEO nanofibre mat prior to chemical treatment is 141 nm with a standard deviation of 29 nm. The average nanofibre diameter of the treated T0.5/1.0Ag/Ca nanofibre mat is 131 nm with a standard deviation of 56 nm. The average nanofibre diameter of the treated T1.0/1.0Ag/Ca nanofibre mat is 130 nm with a standard deviation of 68 nm. The average nanofibre diameter of the treated T0.5/5.0Ag/Ca nanofibre mat is 136 nm with a standard deviation of 71 nm. The average nanofibre diameter of the treated T1.0/5.0Ag/Ca nanofibre mat is 134 nm with a standard deviation of 76 nm.

Figure 2:
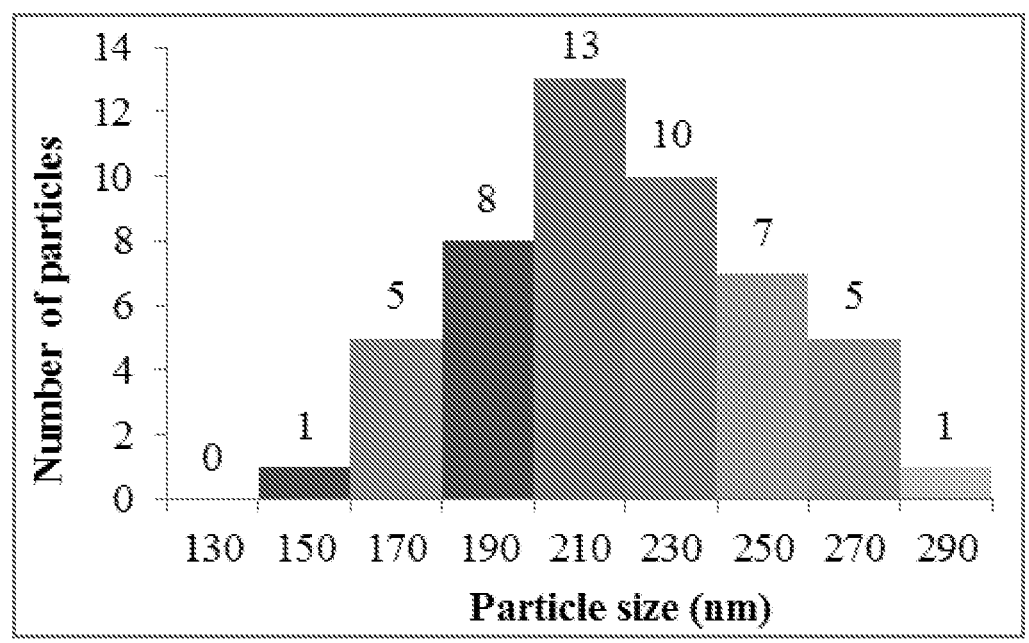
FIG. 2 is a graph depicting average particle size in an antibacterial nanofibre structure.

The SEM images of the treated and untreated nanofibre mats constructed in this example reveal the appearance of particles throughout the mats after treatment. See FIG. 1 (panels A1-E1). As shown in these images, as the concentration of silver in the silver treatment solution increased from 0.5% to 1.0%, so did the particle size. Likewise, as the concentration of calcium in the calcium treatment solution increased from 1% to 5%, so did the particle size. Nanofibre particle sizes were manually measured using a line-drawing feature in ImageJ (ImageJ 2004) software from 50 randomly selected particles in the 10,000× and 20,000× magnification images of the chemically treated samples. FIG. 2 is a graph illustrating the particle size distribution in the four chemically treated nanofibre mats. The average diameter of the measured silver particles is 210 nm with a standard deviation of 32 nm.

EDX analysis was carried out to determine the composition of non-carbon elements in the four sets of chemically treated nanofibre mats, the results of which are shown in Table 2. The percentage of silver in the nanofibres decreases in proportion to an increase in the percentage of calcium (II) ions in the calcium treatment solution.

TABLE 2

Elemental composition in the four sets of silver-alginate nanofibres as determined by EDX.

| Sample | Silver (Ag) | Calcium (Ca) | Sodium (Na) | Chlorine (Cl) | Oxygen (O) |
|---|---|---|---|---|---|
| T0.5/1.0Ag/Ca | 61.42 wt. % | 5.80 wt. % | 4.47 wt. % | 5.24 wt. % | 23.06 wt. % |
| T1.0/1.0Ag/Ca | 59.81 wt. % | 11.7 wt. % | 3.93 wt. % | 8.51 wt. % | 16.04 wt. % |
| T0.5/5.0Ag/Ca | 51.63 wt. % | 11.44 wt. % | 9.03 wt. % | 8.58 wt. % | 19.31 wt. % |
| T1.0/5.0Ag/Ca | 50.56 wt. % | 17.71 wt. % | 2.59 wt. % | 16.98 wt. % | 12.16 wt. % |

Fourier Transform Infrared Spectroscopy (FTIR) was performed to observe the spectral peak variation between the sodium-alginate/PEO nanofibres and the treated alginate nanofibres (samples T0.5/1.0Ag/Ca, T1.0/1.0Ag/Ca, T0.5/5.0Ag/Ca and T1.0/5.0Ag/Ca).

Figure 3A:
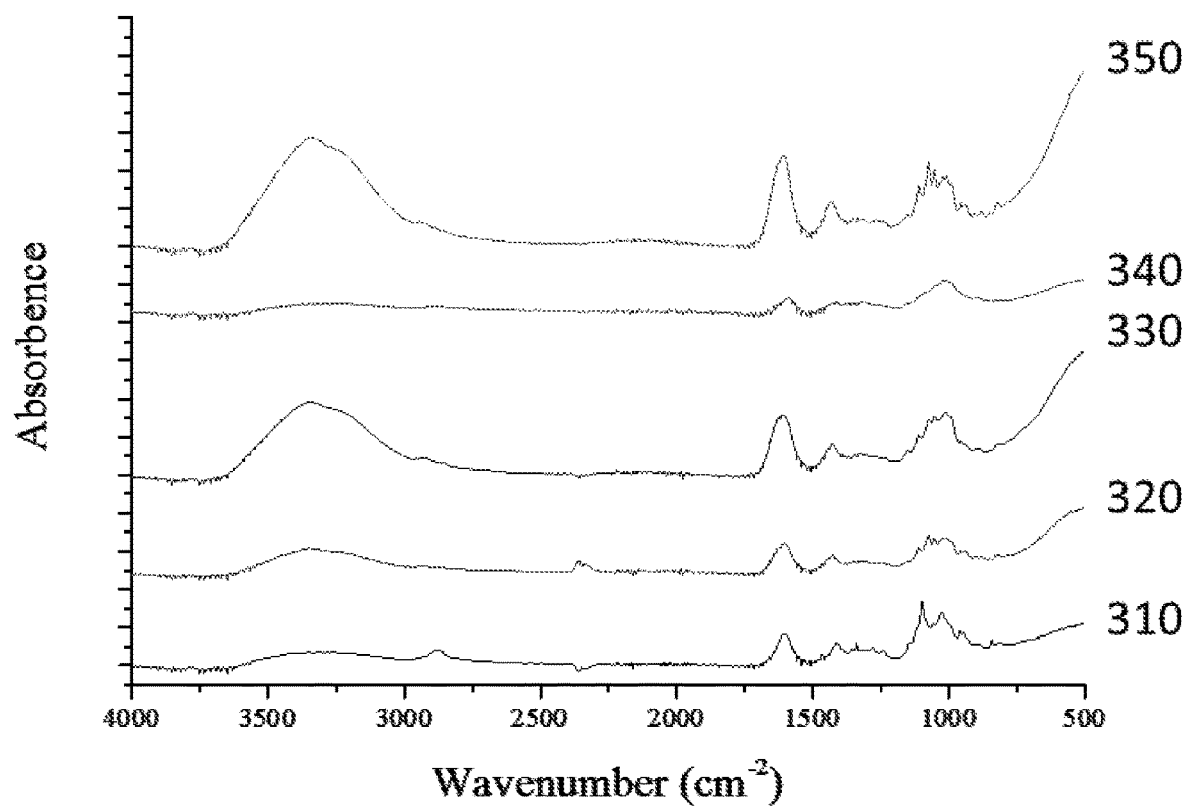
FIG. 3A is an infrared spectra from 4,000 to 400 cm$^{-1}$ of as-spun nanofibre mats before and after chemical treatment.
Figure 3B:
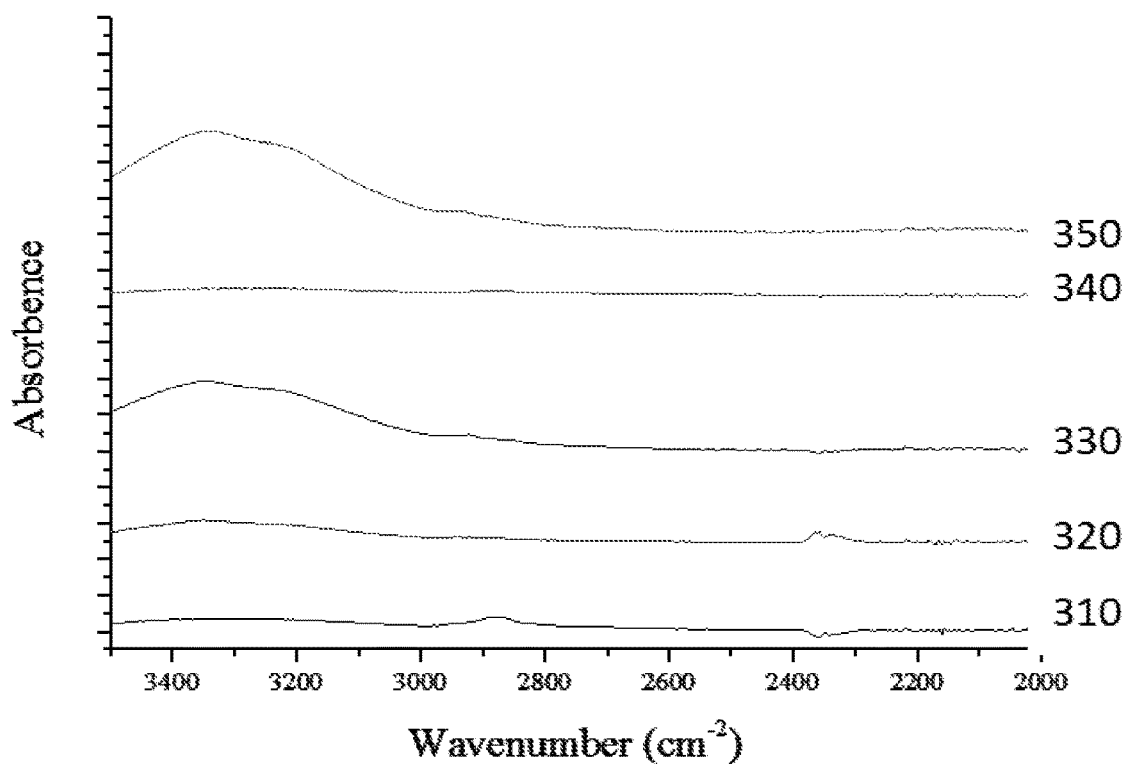
FIG. 3B is an infrared spectra from 3,500 to 2,000 cm$^{-1}$ of the as-spun nanofibre mats before and after chemical treatment.

FTIR spectra from 4,000 to 400 cm$^{-1}$ obtained for the as-spun nanofibre mats before and after chemical treatment is shown in FIG. 3A. Spectra from 3,500 to 2,000 cm$^{-1}$ are shown in FIG. 3B. The spectra include 32 scans at a resolution of 4 cm$^{-1}$.

As shown in FIG. 3B, the peak at 2883 cm$^{-1}$ in the pre-treatment sample (sodium-alginate/PEO nanofibre, 310) represents the —CH$_2$ group from PEO. This peak is diminished or not detectable in the treated samples (320, 330, 340, 350), indicating successful removal of PEO from the treated nanofibres.

The peaks between 3346 and 3336 cm$^{-1}$ correspond to hydrogen bonds of the —OH group. The —OH peak is shifted in the treated samples. The —OH peak in the pre-treatment sample 310 occurs at 3346 cm$^{-1}$. The —OH peak in the T0.5/1.0Ag/Ca sample 320 occurs at 3336 cm$^{-1}$. The —OH peak in the T1.0/1.0Ag/Ca sample 330 occurs at 3340 cm$^{-1}$. The —OH peak in the T0.5/5.0Ag/Ca sample 340 occurs at 3340 cm$^{-1}$. The —OH peak in the T1.0/5.0Ag/Ca sample 350 occurs at 3336 cm$^{-1}$.

The solubility of the chemically modified nanofibre mats was tested in accordance with BS EM 13726-1:2002 section 3.7 dispersion and solubility of hydrogel dressings. Nanofibre mats (0.2 cm×0.2 cm) were placed in a petri-dish in 20 mL of water for 24 hours at 37° C. The mats were visually assessed after 24 hours. Nanofibre mats (0.2 cm×0.2 cm) were similarly placed in a petri-dish in 20 mL of STS comprising 0.4 M NaCl, 0.02 M CaCl$_2$), and 10% newborn calf serum. The nanofibre mats were soaked in STS for 24 hours at room temperature. The fibre content was visually observed to assess nanofibre solubility. The nanofibres remained intact after soaking for 24 hours in water or STS.

Example 2: Preparation of Alginate Nanofibres

Preparation of spinning solution: A 4% by weight 70:30 sodium-alginate/PEO solution for electrospinning was prepared by dissolving 0.7 g sodium-alginate and 0.3 g PEO in 23.875 g distilled water. To improve the homogeneity of the spinning solution, 0.5% by weight Triton™ X-100 was added. A 4% by weight 80:20 sodium-alginate/PEO solution was similarly prepared.

The spinning solution was stored in the dark for 20 days at room temperature and its viscosity measured at days 1, 5, 10 and 20 using a BROOKFIELD viscometer. The viscosity of the sodium-alginate/PEO solution decreased over the period of storage, as such, sodium-alginate/PEO spinning solutions were electrospun within five days of preparation. The viscosities were 2284 cP at day 1, 2184 cP at day 5, 1579 cP at day 10, and 202 cP at day 20.

Electrospinning: A horizontal electrospinning device was used to prepare sodium-alginate nanofibres. The process parameters were set to 12-20 cm working distance, 1.0-0.3 ml/h feed rate, and 9-12 kV applied voltage. The electrospun fibres were collected on aluminum foil. After 1 hour of electrospinning, the foil and deposited fibres were collected and dried for 24 hours at room temperature to remove residual solvents. Process parameters were varied as shown in Table 3. Final process parameters utilized to generate as-spun sodium-alginate/PEO nanofibres were 16 cm working distance, 0.4 ml/hour flow rate and a 10.5 kV applied voltage.

TABLE 3

Electrospinning process parameters to generate sodium-alginate/PEO nanofibres.

| Observation no. | Working distance | Feed rate | Applied voltage | Observations |
|---|---|---|---|---|
| 1 | 16 cm | 0.5 ml/h | 9 kV | Stable jet, uniform deposition but slowly formed droplet |
| 2 | 16 cm | 0.5 ml/h | 10 kV | Stable jet, uniform deposition but slowly formed droplet |
| 3 | 16 cm | 0.5 ml/h | 11 kV | Stable jet, uniform deposition but slowly produced droplets |
| 4 | 16 cm | 0.4 ml/h | 9 kV | Stable jet and uniform deposition but slowly formed droplets |
| 5 | 16 cm | 0.4 ml/h | 10 kV | Stable jet and uniform deposition |
| 6 | 16 cm | 0.4 ml/h | 11 kV | Stable jet and uniform deposition |
| 7 | 16 cm | 0.3 ml/h | 9 kV | Stable jet and uniform deposition but slowly formed droplets |
| 8 | 16 cm | 0.3 ml/h | 10 kV | Stable jet and uniform deposition |
| 9 | 16 cm | 0.3 ml/h | 11 kV | Stable jet, uniform deposition |
| 10 | 16 cm | 0.4 ml/h | 10.5 kV | Stable jet, uniform deposition (Optimized process parameters) |

Characterization of as-spun sodium-alginate/PEO nanofibres: The morphology and structure of the electrospun or as-spun sodium-alginate/PEO nanofibres were observed by SEM. The elemental analysis of the as-spun sodium-alginate/PEO nanofibres was analyzed by FTIR. The solubility of the as-spun sodium-alginate/PEO nanofibres was tested in accordance with BS EN 13726-1:2002 section 3.7 dispersion and solubility of hydrogel dressings. These procedures were performed essentially as described in Example 1.

Figure 4A:
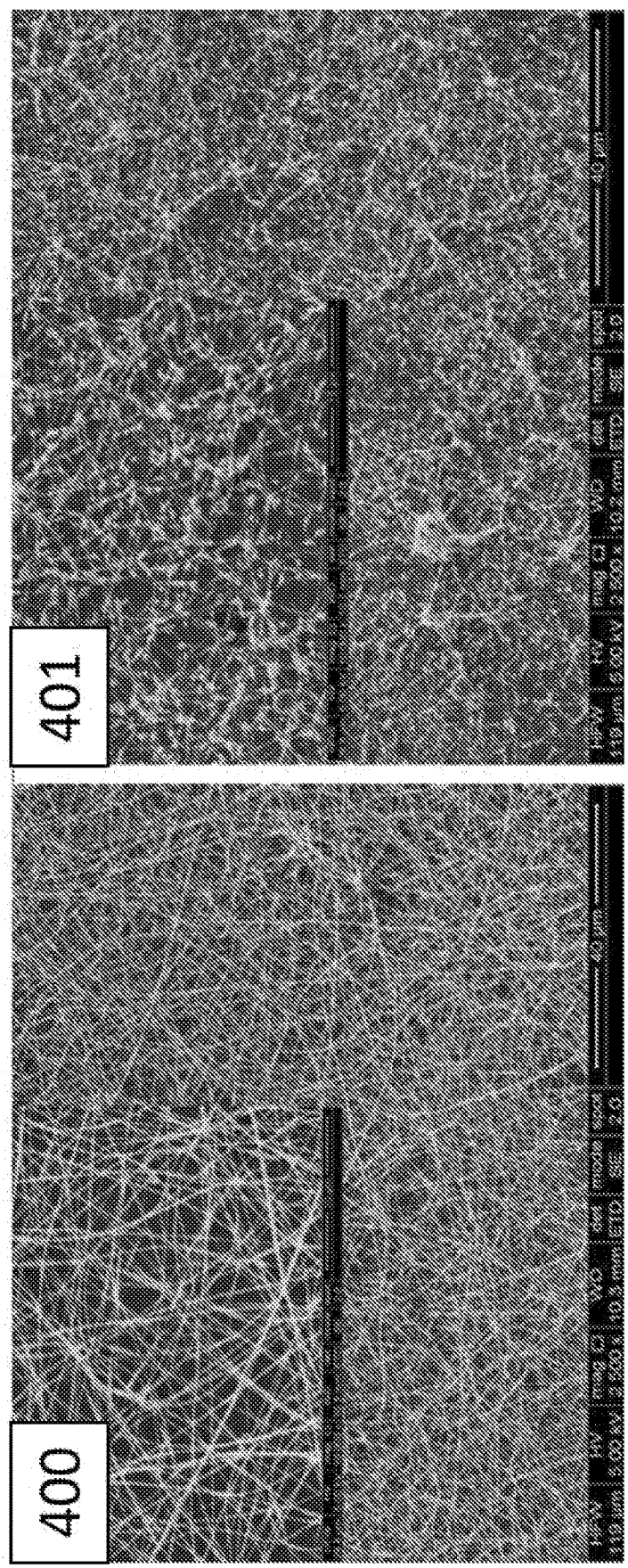
FIG. 4A shows scanning electron microscope images of nanofibres spun from a 70:30 sodium-alginate:PEO solution (400) and a 80:20 sodium-alginate:PEO solution (401).
Figure 4B:
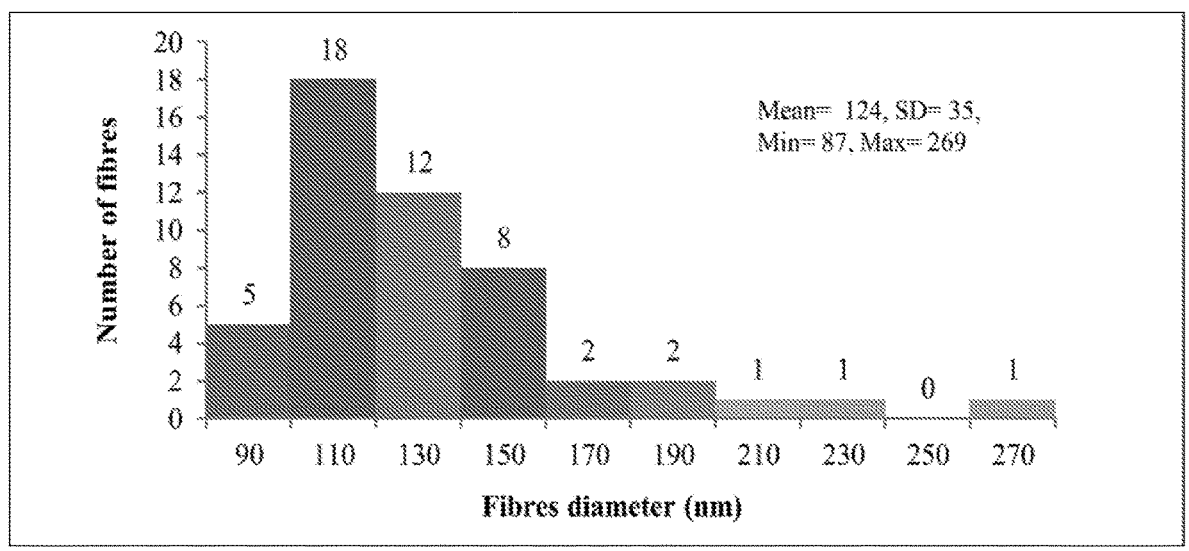
FIG. 4B is a graph illustrating fibre diameter distribution of the nanofibres spun from the 70:30 sodium-alginate:PEO solution as shown in FIG. 4A.

FIG. 4A shows the SEM images of as-spun nanofibres from the 4% by weight 70:30 sodium-alginate:PEO solution (400) and the 4% by weight 80:20 sodium-alginate:PEO solution (401). The average diameter of the as-spun nanofibres from the 4% by weight 70:30 sodium-alginate:PEO solution was 124 nm with a standard deviation of 35 nm, as shown in FIG. 4B. The as-spun nanofibres from the 4% by weight 70:30 sodium-alginate:PEO solution were uniform and bead-free.

Figure 5:
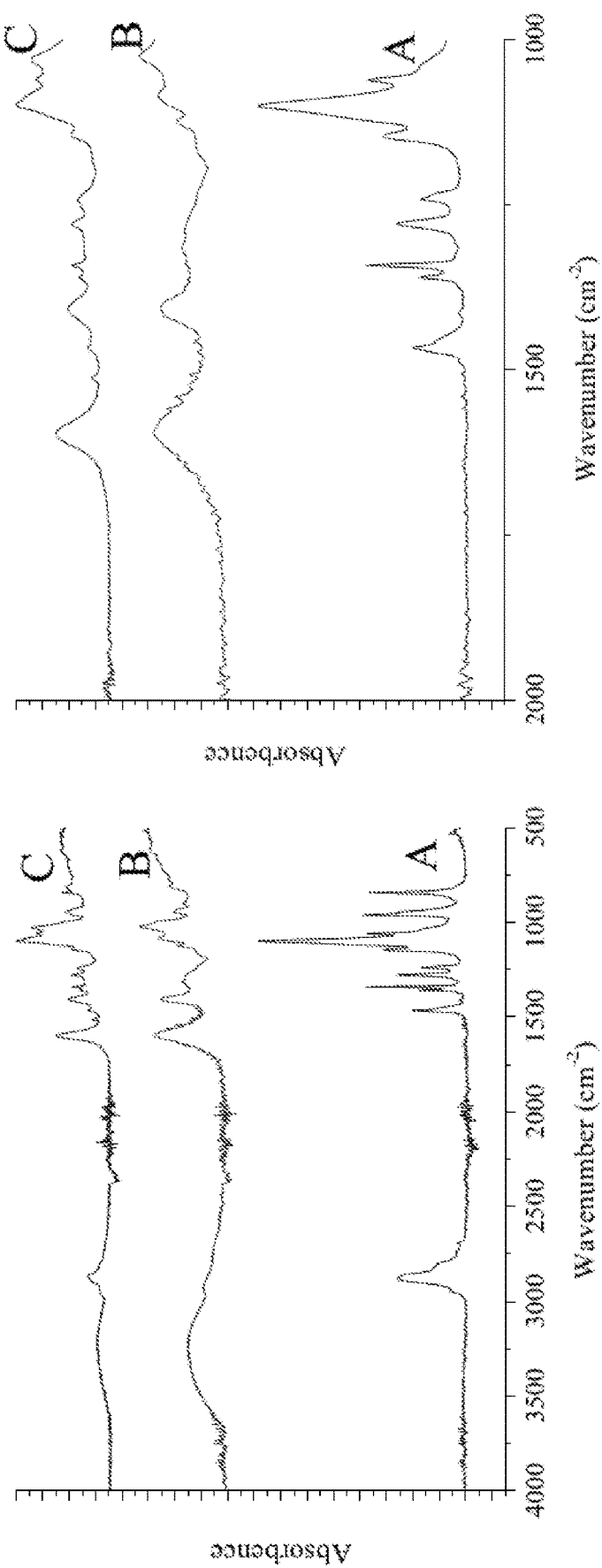
FIG. 5 shows infrared spectra of as-spun PEO nanofibres (A), sodium alginate (B), and sodium alginate/PEO nanofibres (C) within a 4000-400 cm$^{-1}$ and a 2000-1000 cm$^{-1}$ spectral range.

FIG. 5 shows FTIR spectra of pure PEO (panel A), sodium-alginate (panel B) and sodium-alginate/PEO (panel C) nanofibres within a 4000-400 cm$^{-1}$ and 2000-1000 cm$^{-1}$ spectral range. The spectrum for PEO (panel A) has peaks at 1100 cm$^{-1}$ and 843 cm$^{-1}$ corresponding to ether group asymmetric stretch and bending vibrations. The spectra for sodium-alginate (panel B) has peaks at 3336 cm$^{-1}$ corresponding to hydroxyl group stretching, 1593 cm$^{-1}$ for carboxylate group symmetrical stretching and 1410 cm$^{-1}$ for carboxylate group symmetrical stretching. The asymmetrical absorption band for the ether group of PEO was shifted from 1100 cm$^{-1}$ to 1095 cm$^{-1}$ 1 in the sodium-alginate/PEO nanofibre. The asymmetrical absorption band for the carboxylate group of sodium-alginate was shifted from 1593 cm$^{-1}$ to 1612 cm$^{-1}$ in the sodium-alginate/PEO nanofibre.

The solubility of the as-spun sodium-alginate/PEO nanofibres in water and STS were assessed as in Example 1. The nanofibres dissolved in either water or STS within 2 to 3 minutes of soaking.

Example 3: Construction of a Composite Dressing Structure Comprising As-Spun Alginate Nanofibres Electrospun nanofibres, such as those prepared in Example 2, were deposited on the surface of a Na-CMC nonwoven base.

Figure 6:
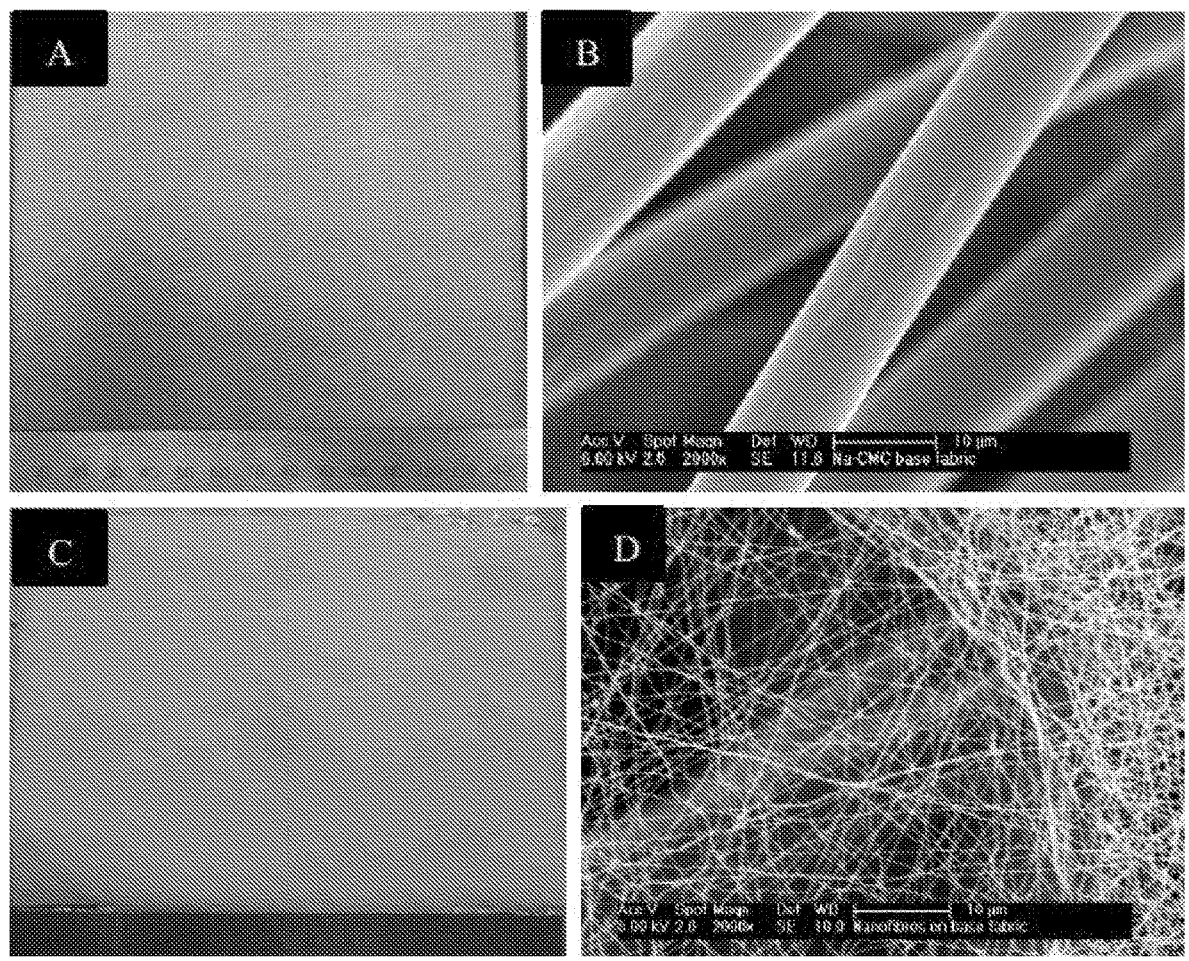
FIG. 6 shows photographs and scanning electron microscope images of a base fabric before and after deposition of as-spun nanofibres.

100971 A Na-CMC nonwoven fabric was applied to a collector in an electrospinning device and a 4% by weight 70:30 sodium-alginate/PEO solution was electrospun as described in Example 2. The Na-CMC fabric was deposited with sodium-alginate/PEO nanofibres to generate a composite dressing structure. The morphology of as-spun nanofibres deposited on foil and on Na-CMC was visualized by SEM, as shown in FIG. 6 (panels A-D). FIG. 6, panel A shows a photograph of the Na-CMC base fabric, panel B shows a SEM image of the Na-CMC base fabric, panel C shows a photograph of the Na-CMC base fabric deposited with as-spun sodium-alginate/PEO nanofibres, and panel D shows a SEM image of the Na-CMC base fabric deposited with as-spun sodium-alginate/PEO nanofibres. These images indicate no morphological difference between the Na-CMC fabric before and after deposition of as-spun nanofibres to its surface.

Example 4: Antibacterial Nanofibrous Dressing Structure

The composite dressing structure of Example 3 was chemically treated to generate an antibacterial nanofibrous dressing structure.

A 10 cm×10 cm composite dressing structure of Example 3 was soaked in a petri-dish containing ethanol absolute for 10 minute with gentle shaking to dissolve PEO. The ethanol washed sample was transferred to a petri-dish containing a calcium solution (1.0% or 5% by weight $CaCl_2$) in ethanol absolute) and allowed to soak for 10 minutes. During this calcium treatment step, an ion exchange reaction occurred between the sodium (I) ions from sodium-alginate nanofibres and calcium (II) ions from the calcium solution to generate insoluble calcium-alginate nanofibres. Similarly, sodium (I) ions from the Na-CMC fabric may exchange with calcium (II) ions from the calcium solution. The sample was then transferred to a petri-dish containing a silver solution (0.5% or 1% by weight $AgNO_3$ in ethanol absolute) and allowed to soak for 10 minutes. During this silver treatment step, an ion exchange reaction occurred between sodium (I) ions from sodium-alginate nanofibres, calcium (II) ions from calcium-alginate and silver (I) ions from the silver solution to generate nanofibres having sodium-alginate, calcium-alginate and silver-alginate. Similarly, sodium (I) ions from the Na-CMC fabric and calcium (II) ions from Ca-CMC fabric may exchange with silver (I) ions from the silver solution. The sample was then washed in ethanol absolute to remove precipitated and unreacted salts. The sample was dried at room temperature (about 20° C.).

This process was repeated using different concentrations of $CaCl_2$) and $AgNO_3$ as shown in Table 1. FIG. 1 (panels B1-E1) show SEM images showing the morphology of nanofibres deposited on a Na-CMC backing following treatment with calcium and silver treatment solutions.

Figure 7:
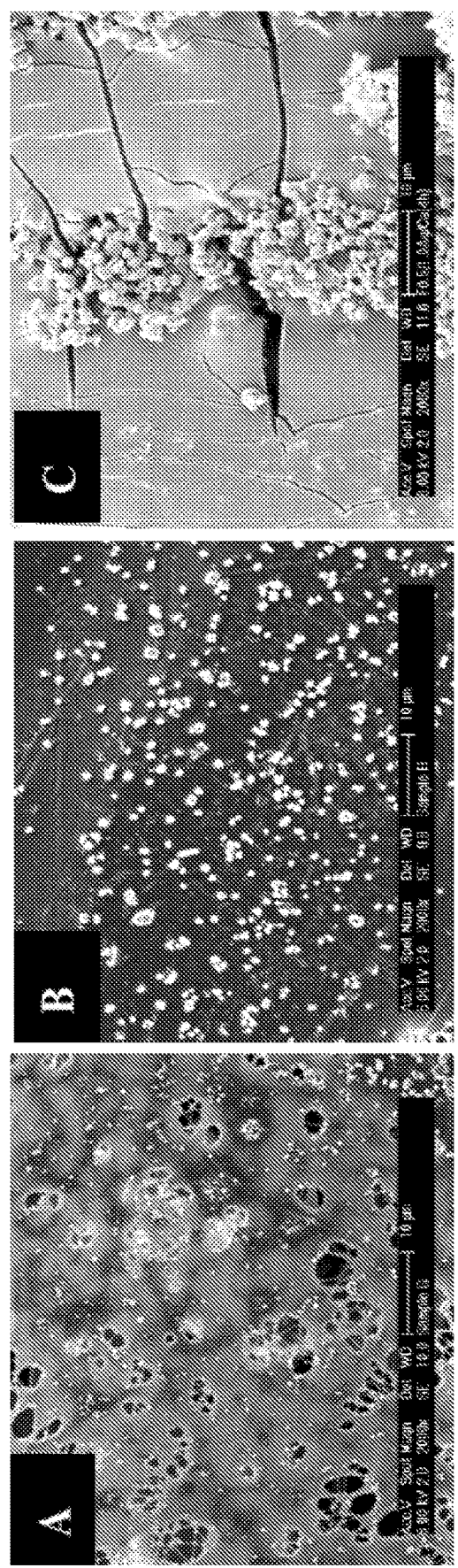
FIG. 7 shows scanning electron microscope images of nanofibres electrosprayed with a malodor absorbing agent for different periods of time.

Example 5: Antibacterial Nanofibrous Dressing Structure Deposited with a Malodor Absorbing Agent by Electrospraying Antibacterial nanofibrous dressing structures prepared in Example 4 were electrosprayed with the malodor absorbing agent hydroxypropyl-P-cyclodextrin (HP-β-CD). FIG. 7 shows images of nanofibrous dressing structures prepared using a 1.0% $CaCl_2$) solution and a 0.5% $AgNO_3$ solution.

Electrospraying process parameters were adjusted to 0.5-2 ml/h feed rate, 7-15 kV applied voltage and 12-20 cm working distance to obtain uniform dispersion of HP-β-CD particles on a collector comprising aluminum foil. Electrosprayed HP-β-CD particles collected on aluminum foil were dried and characterized to optimize process parameters. The electrospraying process was optimized at 1.0 ml/h feed rate, 12 kV applied voltage and 16 cm working distance.

HP-β-CD particles were deposited on the antibacterial nanofibrous dressing structures prepared in Example 4 using optimized process parameters. FIG. 7 (panels A-C) show SEM images showing the surface morphology of the electrosprayed nanofibrous dressings of Example 4. The dressing shown in FIG. 7, panel A was electrosprayed for 1 hour, the dressing shown in panel B was electrosprayed for 2 hours, and the dressing shown in panel C was electrosprayed for 4 hours.

Example 6: Antibacterial Nanofibrous Dressing Structure Deposited with a Malodor Absorbing Agent by Electrospinning Antibacterial nanofibrous dressing structures prepared in Example 4 are combined with the malodor absorbing agent hydroxypropyl-β-cyclodextrin (HP-β-CD) by electrospinning a HP-β-CD solution onto the nanofibrous surface of the dressing structures. The HP-β-CD solution comprises the carrier polymer PEO.

A series of spinning solutions having 4-12% by weight 50:50 HP-β-CD:PEO were prepared in water. Another series of spinning solutions having 8% by weight 50:50 to 90:10 HP-β-CD:PEO were prepared in water.

Electrospinning process parameters were adjusted to 0.5-2.5 ml/h feed rate, 5-11 kV applied voltage and 8-16 cm working distance to obtain smooth fibres. Electrospun HP-β-CD particles were collected on aluminum foil, dried for 24 hours, and characterized to optimize process parameters. The electrospraying process was optimized at 1.0 ml/h feed rate, 12 kV applied voltage and 16 cm working distance.

Electrospinning of HP-β-CD/PEO was carried out with varying mass ratios and concentrations at 1 ml/h feed rate, 12 cm working distance, and 7 kV applied voltage to obtain smooth nanofibres. Table 4 provides spinning solution compositions and properties of HP-β-CD/PEO electrospun nanofibres deposited on foil.

TABLE 4

Summary of electrospun HP-β-CD/PEO fibre characteristics.

| Polymer conc. (% wt.) | HP-β-CD/PEO ratio | Fibre diameter range (nm) | Average diameter (nm) | Fibre morphology | Diameter of nanofibres web (cm) |
|---|---|---|---|---|---|
| 8 | 50:50 | 240-289 | 264 | Smooth fibres | 9.2 |
| 8 | 60:40 | 189-301 | 244 | Smooth fibres | 10.5 |
| 8 | 70:30 | 128-390 | 236 | Few beads | 15.5 |
| 8 | 80:20 | 80-1628 | 208 | Mainly beads | — |
| 8 | 90:10 | — | — | Mainly beads | — |
| 4 | 50:50 | 60-972 | 268 | Mainly beads | — |
| 6 | 50:50 | 177-362 | 248 | Smooth fibres | 12.5 |
| 8 | 50:50 | 240-289 | 264 | Smooth fibres | 9.2 |
| 10 | 50:50 | 194-302 | 254 | Smooth fibres | 7.4 |
| 12 | 50:50 | 128-328 | 281 | Branched fibres | 5.7 |

Figure 8:
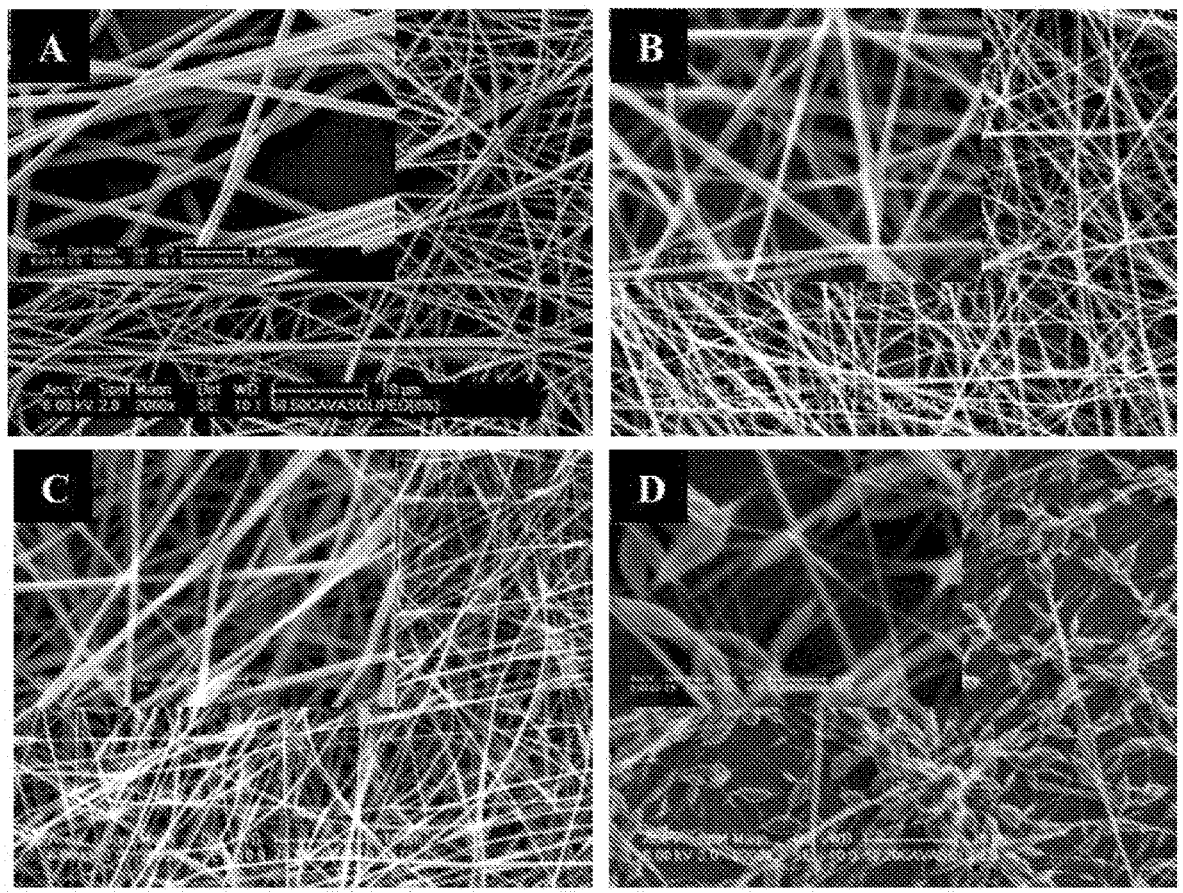
FIG. 8 shows a scanning electron microscope image of fibres electrospun from a solution having a blend of HP-β-CD/PEO.

The morphology of the electrospun HP-β-CD/PEO fibres is shown in the SEM images (2,000×, insert 10,000×) of FIG. 8 (panels A-D). The fibres in FIG. 8 were electrospun from an 8% solution having 50:50 (panel A), 60:40 (panel B), 70:30 (panel C), and 80:20 (panel D) HP-β-CD/PEO blend rations.

Electrospun HP-β-CD particles are collected on a nanofibrous dressing structure of Example 4 using the optimized process parameters.

Example 7: Dressing Structure Comprising Antibacterial Nanofibres

Figure 9:
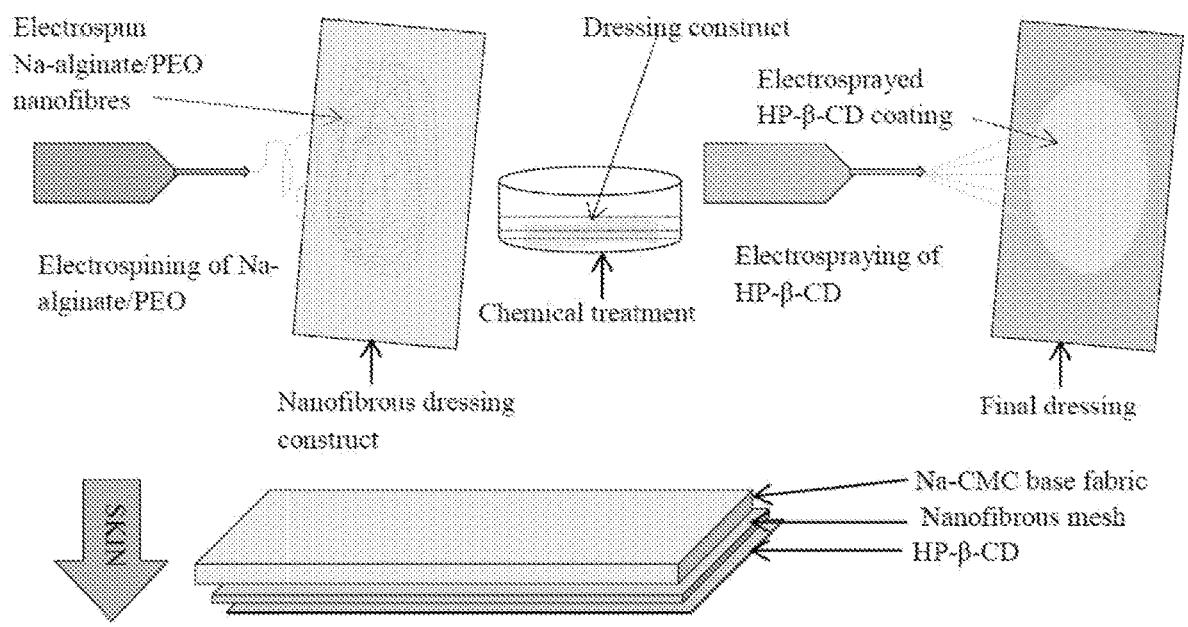
FIG. 9 provides an example workflow for the preparation of a dressing structure comprising nanofibres.

A scheme of a proposed dressing structure is shown in FIG. 9. Electrospun nanofibres, such as those prepared in Example 2, are deposited on the surface of a backing to generate a nanofibrous dressing construct using the method described in Example 3. The dressing construct is chemically treated as in Example 4 to generate an antibacterial nanofibrous dressing structure. The antibacterial nanofibrous dressing construct is electrosprayed with HP-β-CD as described in Example 5 to generate the final dressing. The final dressing structure comprises a sodium-CMC base fabric, a nanofibrous mesh comprising antibacterial silver-alginate, and a HP-β-CD coating.

Figure 10:
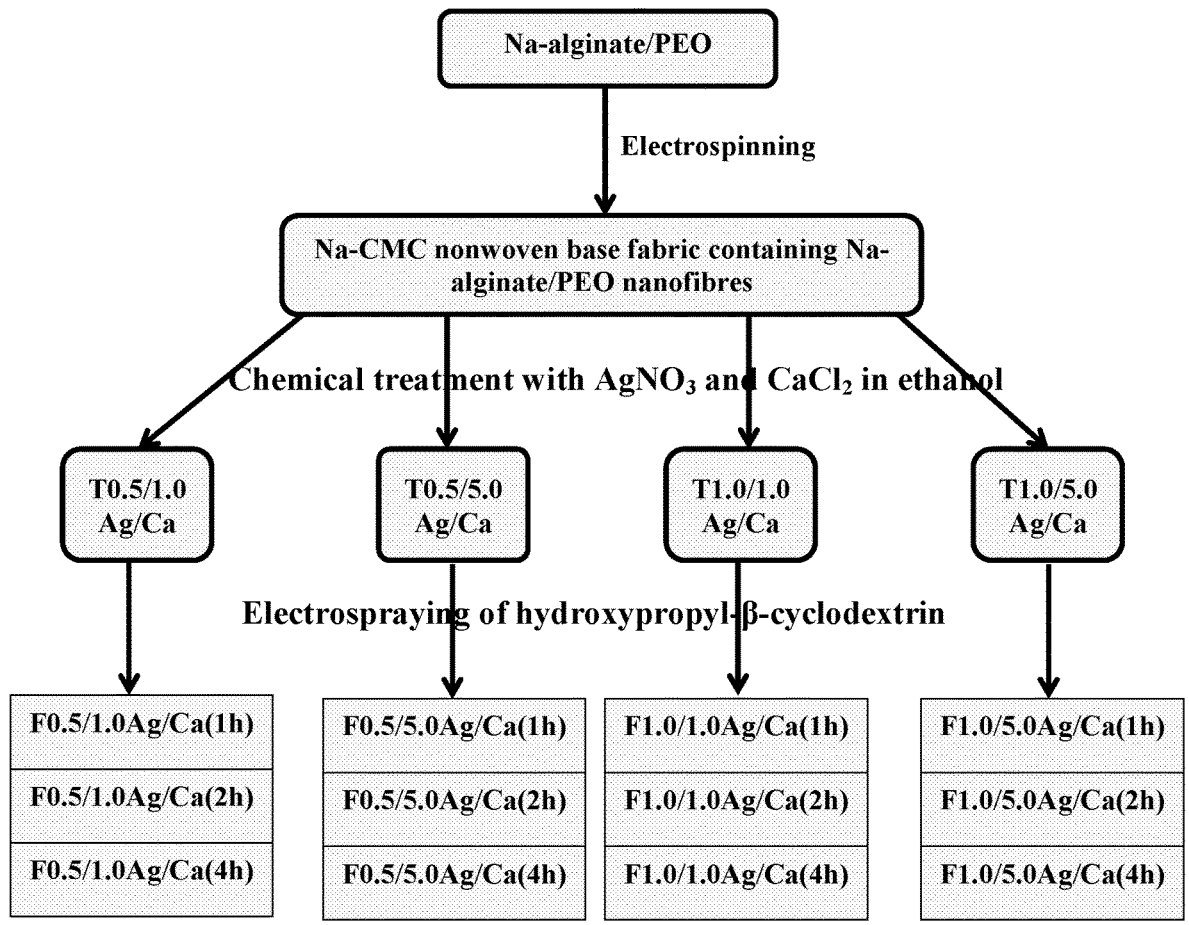
FIG. 10 provides a summary of example methods for the preparation of a nanofibrous structure.
Figure 10:
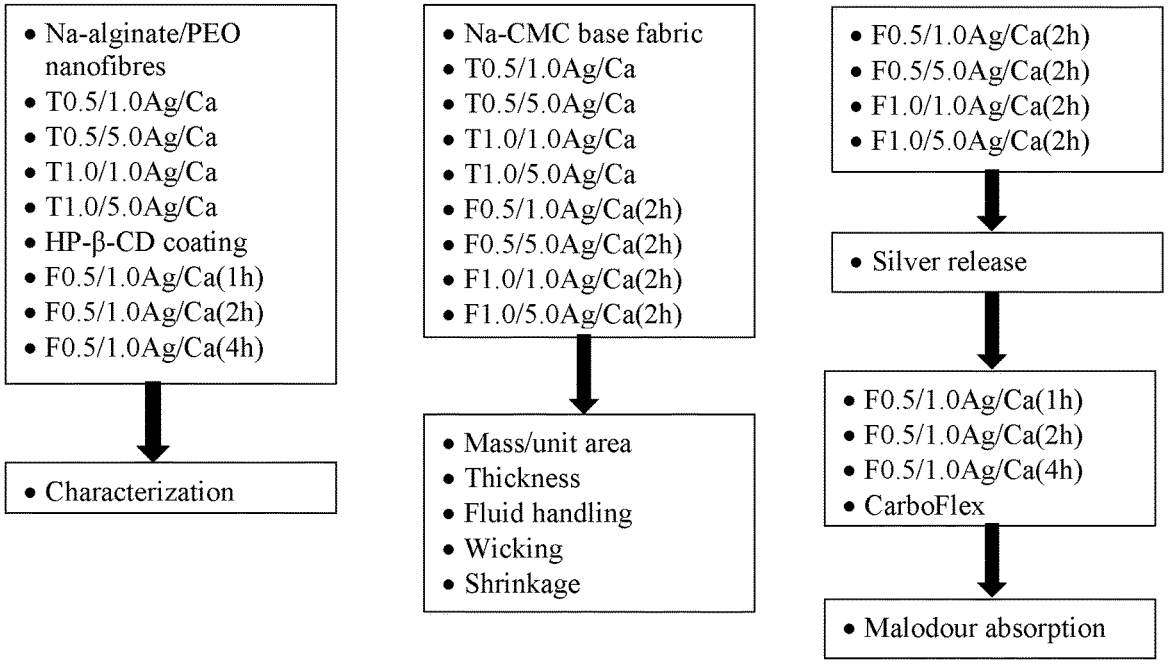

Example 8: Methods for Preparing Dressing Structures Comprising Antibacterial Nanofibres A schematic summarizing the methods described in Example 1 through Example 7 is provided in FIG. 10.

Example 9: Assessment of Dressing Structures and Dressing Structure Components

Compositions produced by the methods described in Examples 1 through 7 are summarized in Table 5.

TABLE 5

Summary of wound dressing compositions.

| Tests | Set | Sets of samples |
|---|---|---|
| Mass per unit area | Set -1 | Base fabric |
| Thickness | | Chemically treated (T0.5/1.0Ag/Ca) sample |
| Fluid absorption and retention | | Final (F0.5/1.0Ag/Ca(2 h)) sample |
| Lateral wicking | Set -2 | Base fabric |
| Shrinkage | | Chemically treated (T0.5/5.0Ag/Ca) sample |
| | | Final (F0.5/5.0Ag/Ca(2 h)) sample |
| | Set -3 | Base fabric |
| | | Chemically treated (T1.0/1.0Ag/Ca) sample |
| | | Final (F1.0/1.0Ag/Ca(2 h)) sample |
| | Set -4 | Base fabric |
| | | Chemically treated (T1.0/0.5Ag/Ca) sample |
| | | Final (F1.0/0.5Ag/Ca(2 h)) sample |

The average mass per unit area of the dressing compositions were assessed in accordance with BS EN 12127:1998 test method. Table 6 presents the average mass per 100 cm$^2$ for different compositions. The mass per unit area increased in the chemically treated compositions compared to the base fabric.

TABLE 6

Mass per unit area of wound dressing compositions.

| Sample | Mass/unit area (g/100 cm$^2$) | % +/− respect to base fabric |
|---|---|---|
| Base fabric | 1.043 | — |
| T0.5/1.0Ag/Ca | 1.096 | +5.08% |
| F0.5/1.0Ag/Ca(2 h) | 1.320 | +26.55% |
| T0.5/5.0Ag/Ca | 1.384 | +32.69% |
| F0.5/5.0Ag/Ca(2 h) | 1.429 | +37% |
| T1.0/1.0Ag/Ca | 1.111 | +6.51% |
| F1.0/1.0Ag/Ca(2 h) | 1.398 | +34.03% |
| T1.0/5.0Ag/Ca | 1.856 | +77.94% |
| F1.0.5.0Ag/Ca(2 h) | 1.906 | +82.74% |

The thickness of the dressing compositions were assessed in accordance with BS EN ISO 9073-2:1997. The tests were carried out with 0.0 weight (without additional weight, i.e. normal state of the tester) and 100 g weight (with 100 g known weight). Table 7 presents the average thickness and relative changes in the thickness of different compositions. The addition of a HP-β-CD coating to a dressing composition increased the overall dressing composition thickness. Calcium had an effect on composition thickness.

TABLE 7

Average thickness of wound dressing compositions.

| Sample | Thickness (mm) at 0.0 wt. | % +/− respect to base dressing | Thickness (mm) at 100 g wt. | % +/− respect to base fabric | Difference between 0.0 wt. and 100 g wt. |
|---|---|---|---|---|---|
| Base dressing | 1.550 | — | 1.083 | — | −30% |
| T0.5/1.0Ag/ca | 1.633 | +5.35% | 1.167 | +7.75% | −29% |
| F0.5/1.0Ag/Ca(2 h) | 1.967 | +26.9% | 1.383 | +27.7% | −30% |
| T0.5/5.0Ag/Ca | 1.883 | +21.48% | 1.667 | +53.92% | −12% |
| F0.5/5.0Ag/Ca(2 h) | 2.133 | +37.6% | 1.700 | +56.97% | −20% |
| T1.0/1.0Ag/Ca | 1.650 | +6.45% | 1.233 | +13.85% | −25% |
| F1.0/1.0Ag/Ca(2 h) | 1.800 | +16.1% | 1.417 | +30.84% | −21% |
| T1.0/5.0Ag/Ca | 1.883 | +21.48% | 1.583 | +46.16% | −16% |
| F1.0/5.0Ag/Ca(2 h) | 2.133 | +37.6% | 1.750 | +61.58% | −18% |

The average absorption and retention properties of the wound dressing compositions were determined in accordance with BS EN 13726-1:2002 section 3.2 free swell absorptive capacity. Absorption refers to how much fluid is absorbed by each composition. Retention refers to how much of the fluid is retained in the composition under a certain pressure. Table 8 provides a summary of the fluid handling properties of the wound dressing compositions. The average absorption and retention of the base fabric were found to be higher than the chemically treated compositions and the final dressings. The concentrations of silver and calcium ions during chemical treatment negatively affected the absorption and retention ability of compositions.

TABLE 8

Absorption and retention of fluids in wound dressing compositions.

| Sample | Absorption (g/g) | Retention (g/g) | % Retention* | Absorption (g/100 cm$^2$) | Retention (g/100 cm$^2$) |
|---|---|---|---|---|---|
| Base fabric | 17.50 | 11.85 | 67.72 | 18.01 | 12.2 |
| T0.5/1.0Ag/Ca | 14.58 | 10.03 | 68.8 | 15.97 | 10.98 |
| F0.5/1.0Ag/Ca(2 h) | 14.37 | 8.10 | 56.37 | 18.97 | 10.7 |
| T0.5/5.0Ag/Ca | 13.77 | 7.95 | 57.74 | 19.06 | 11 |
| F0.5/5.0Ag/Ca(2 h) | 12.23 | 6.79 | 55.52 | 17.47 | 9.7 |
| T1.0/1.0Ag/Ca | 14.84 | 8.36 | 56.34 | 16.48 | 9.28 |
| F1.0/1.0Ag/Ca(2 h) | 13.24 | 7.47 | 56.42 | 18.5 | 10.45 |
| T1.0/0.5Ag/Ca | 8.73 | 5.42 | 62.09 | 16.21 | 10.07 |
| F1.0/5.0Ag/Ca(2 h) | 11.03 | 6.30 | 57.12 | 20.97 | 11.97 |

*% Retention = [Retention (g/g)/Absorption (g/g) × 100]

Vertical wicking of the wound dressing compositions was tested in accordance with BS 3424-18:1986 standard test method. Table 9 provides a summary of the wicking behavior of the wound dressing compositions. The average wicking height of the compositions treated with calcium and silver solutions was higher than the average wicking height of the base fabric. The addition of HP-β-CD had little or negligible effect on the average wicking height of a composition.

TABLE 9

Lengthwise and traverse wicking test for wound dressing compositions.

| Sample | Lengthwise (mm) | Transverse (mm) | Average (mm) |
|---|---|---|---|
| Base fabric | 18.67 | 18.00 | 18.34 |
| T0.5/1.0AgCa | 25.67 | 28.67 | 27.17 |
| F0.5/1.0AgCa(2 h) | 27.67 | 28.67 | 28.17 |
| T0.5/5.0AgCa | 38.67 | 45.33 | 42 |
| F0.5.5.0AgCa(2 h) | 39.67 | 47.00 | 43.33 |
| T1.0.1.0AgCa | 26.33 | 27.67 | 27 |
| F1.0/1.0AgCa(2 h) | 25.67 | 27.67 | 26.67 |
| T1.0/5.0AgCa | 45.00 | 46.00 | 45.5 |
| F1.0/5.0AgCa(2 h) | 46.00 | 51.33 | 48.66 |

The shrinkage behavior of the wound dressing compositions was assessed. Table 10 provides the area shrinkage of wound dressing compositions. Electrospraying HP-β-CD on a composition had a positive effect on the dimensional stability of that composition. The concentration of calcium in the chemical treatment process negatively affected the dimensional stability of the wound dressing compositions.

TABLE 10

Area shrinkage of hydrated and dried wound dressing compositions.

| Sample | Hydrated (%) | Dried (%) |
|---|---|---|
| Base fabric | 31.27 | 46.83 |
| T0.5/1.0Ag/Ca | 31.27 | 62.54 |
| F0.5/1.0Ag/Ca(2 h) | 33.27 | 36.08 |
| T0.5/5.0Ag/Ca | 20.50 | 43.85 |
| F0.5/5.0Ag/Ca(2 h) | 24.92 | 38.66 |
| T1.0/1.0Ag/Ca | 27.75 | 55.16 |
| F1.0/1.0Ag/Ca(2 h) | 28.45 | 35.33 |
| T1.0/5.0Ag/Ca | 15.98 | 24.16 |
| F1.0/5.0Ag/Ca(2 h) | 25.58 | 29.23 |

Example 10: Silver-Release from Antibacterial Dressing Structures

The antibacterial nanofibrous dressing structures electrosprayed with HP-β-CD from Example 5 were tested for their silver-release properties. A 2 cm×2 cm sample of each dressing structure was immersed in 20 mL of solution A (0.4 M NaCl, 0.02 M $CaCl_2$, distilled water) in a glass bottle and incubated at 37° C. for 7 days. 10 mL samples of the solution were withdrawn at 24 intervals during the incubation period. A fresh 10 mL aliquot of solution A was supplemented to the incubated sample each time a sample was drawn. The silver content in the withdrawn samples was determined using Inductively Coupled Plasma-Optical Emission Spectroscopy (ICP-OES). The amount of silver released from each dressing structure is shown in Table 11.

TABLE 11

Silver release from antibacterial dressing structures.

| Sample no. | Sample Size | Silver release amount (ppm) | | | | | | |
|---|---|---|---|---|---|---|---|---|
| | | 1-day | 2-day | 3-day | 4-day | 5-day | 6-day | 7-day |
| F0.5/1.0AG/Ca(2 h) | 20 | 1.4 | 1.6 | 1.1 | 1.1 | 1.0 | 1.0 | 1.0 |
| F0.5/5.0AG/Ca(2 h) | | 1.5 | 1.5 | 1.4 | 1.3 | 1.4 | 1.3 | 1.4 |
| F1.0/1.0AG/Ca(2 h) | | 1.4 | 1.4 | 1.4 | 1.4 | 1.4 | 1.4 | 1.4 |
| F1.0/5.0AG/Ca(2 h) | | 1.4 | 1.5 | 1.5 | 1.5 | 1.5 | 1.5 | 1.5 |

Example 11: Malodor Absorbency of Antibacterial Dressing Structures

The antibacterial nanofibrous dressing structures electro electrosprayed with HP-β-CD from Example 5 were tested for their ability to absorb malodors. Dressing structure samples (2 cm×2 cm) were exposed to a malodorous environment comprising 0.5 ml of a stimulated test solution (0.4 M NaCl, 0.02 M $CaCl_2$, 10% newborn calf serum, 2% diethylamine). A sample of a commercial product was similarly tested (CarboFLEX®, ConvaTec). Ten randomly selected individuals assessed the smell intensity of each sample by rating the smell from 0 to 10. A score of 0 indicated "no smell" and a score of 10 indicated "maximum smell". The results of the smell assessment for dressing structures is shown in Table 12. Samples which were electrosprayed with HP-β-CD for longer periods of time (4 hours versus 1 or 2 hours) had lower smell ratings.

TABLE 11

Malodor absorbency of antibacterial dressing structures electrosprayed with HP-β-CD.

| Dressing sample | Rating (1 day incubation time) | Rating (7 days incubation time) | Specification (Level of malodour) | Grade |
|---|---|---|---|---|
| F0.5/1.0Ag/Ca(1 h) | 6.9 | 7.5 | Moderate | Fair |
| F0.5/1.0Ag/Ca(2 h) | 6.1 | 6.6 | Moderate | Fair |
| F0.5/1.0Ag/Ca(4 h) | 5.1 | 4.7 | Minimal | Good |
| CarboFlex | 4.3 | 4.9 | Minimal | Good |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. Anti-odor, antimicrobial nanofibers comprising a) alginate nanofibers electrospun from an aqueous solution, the aqueous solution comprising a 4% mixture of alginate:poly (ethylene)oxide in a 70:30 ratio; b) an antimicrobial agent; c) a malodor absorbing agent, and d) calcium present in the anti-odor, antimicrobial nanofibers at a concentration of no more than 20%, and e) oxygen present in the anti-odor, antimicrobial nanofibers at a concentration from about 10% to about 25%, wherein the malodor absorbing agent is deposited via electrospraying, electrospinning, or both electrospraying and electrospinning onto a surface of the anti-odor, antimicrobial nanofibers.

2. The anti-odor, antimicrobial nanofibers of claim 1, wherein the antimicrobial agent comprises silver, silver ions, acetic acid, chlorhexidine, iodine, hydrogen peroxide, sodium hypochlorite, potassium permanganate, triclosan, an antibiotic, or a combination thereof.

3. The anti-odor, antimicrobial nanofibers of claim 1, wherein an average nanofiber diameter is from 120 nm to 150 nm.

4. The anti-odor, antimicrobial nanofibers of claim 1, further comprising a surfactant.

5. The anti-odor, antimicrobial nanofibers of claim 4, wherein the surfactant is chosen from the group consisting of octoxynol, polysorbate, stearyl alcohol, sorbitan, polyglycerol, polyricinoleate, poloxamer, pentaethylene glycol monododecyl ether, oleyl alcohol, octyl glucoside, N-octyl beta-D-thioglycopyranoside, octaethylene glycol monododecyl ether, nonyl phenoxypolyethoxylethanol, nonoxynols, octylphenoxypolyethoxyethanol, monolaurin, ethoxylate, lauryl glucoside, isoceteth-20, decyl glucoside, cetomacrogol, cetostearyl alcohol, cetyl alcohol, cocamide diethanolamine, cocamide monoethyl phthalate, and derivatives and combinations thereof.

* * * * *